United States Patent [19]
Kitazawa et al.

[11] Patent Number: 6,133,266
[45] Date of Patent: Oct. 17, 2000

[54] 3,4-DISUBSTITUTED PHENYLETHANOLAMINO-TETRALINCARBOXAMIDE DERIVATIVES

[75] Inventors: Makio Kitazawa; Kosuke Okazaki; Tetsuro Tamai; Masaru Saito; Nobuyuki Tanaka; Hiroaki Kobayashi; Ken Kikuchi; Hideyuki Muranaka, all of Nagano, Japan

[73] Assignee: Kissei Pharmaceutical Co., Ltd., Nagano, Japan

[21] Appl. No.: 09/125,429

[22] PCT Filed: Feb. 18, 1997

[86] PCT No.: PCT/JP97/00424

§ 371 Date: Feb. 10, 1999

§ 102(e) Date: Feb. 10, 1999

[87] PCT Pub. No.: WO97/30023

PCT Pub. Date: Aug. 21, 1997

[30] Foreign Application Priority Data

Feb. 19, 1996 [JP] Japan .................................. 8-068885

[51] Int. Cl.[7] ...................... A61K 31/165; A61K 31/535; C07C 235/06; C07D 295/192
[52] U.S. Cl. ...................... 514/237.5; 514/620; 544/165; 546/206; 548/540; 564/165; 564/172
[58] Field of Search ............................. 544/165; 564/165, 564/172; 514/237.5

[56] References Cited

FOREIGN PATENT DOCUMENTS 6-506676 7/1994 Japan .
6-506955 8/1994 Japan .

OTHER PUBLICATIONS

Tamai et al, Chemical Abstracts, vol. 130, No. 196510, 1999.

Primary Examiner—Robert W. Ramsuer
Attorney, Agent, or Firm—Sughrue, Mion, Zinn, Macpeak & Seas, PLLC

[57] ABSTRACT

The present invention relates to 3,4-disubstituted phenylethanolaminotetralincarboxamide derivatives represented by the general formula:

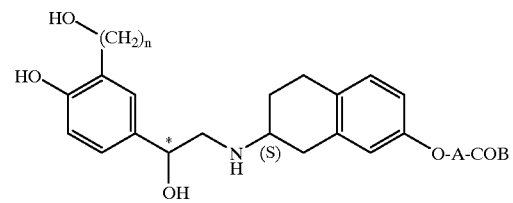

(wherein A represents a lower alkylene group; B represents an amino group, a di(lower alkyl)amino group or a 3 to 7-membered alicyclic amino group which may contain an oxygen atom in the ring; n is an integer of 1 or 2; the carbon atom marked with * represents a carbon atom in R configuration, S configuration or a mixture thereof; and the carbon atom marked with (S) represents a carbon atom in S configuration) and pharmaceutically acceptable salts thereof, which have a selective $\beta_2$-adrenergic receptor stimulating effect with relieved burdens on the heart such as tachycardia and are useful as an agent for the prevention of threatened abortion and premature labor, a bronchodilator and an agent for pain remission and stone removal in urolithiasis.

10 Claims, No Drawings

3,4-DISUBSTITUTED PHENYLETHANOLAMINO-TETRALINCARBOXAMIDE DERIVATIVES

This application is a 371 of PCT/JP97/00424 filed Feb. 18, 1997.

TECHNICAL FIELD

The present invention relates to novel 3,4-disubstituted phenylethanolaminotetralincarboxamide derivatives which are useful as medicaments.

More particularly, the present invention relates to 3,4-disubstituted phenylethanolaminotetralincarboxamide derivatives represented by the general formula:

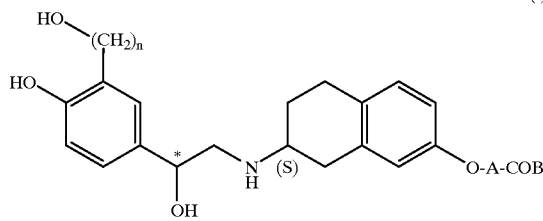

(wherein A represents a lower alkylene group; B represents an amino group, a di(lower alkyl)amino group or a 3 to 7-membered alicyclic amino group which may contain an oxygen atom in the ring; n is an integer of 1 or 2; the carbon atom marked with * represents a carbon atom in R configuration, S configuration or a mixture thereof; and the carbon atom marked with (S) represents a carbon atom in S configuration) and pharmaceutically acceptable salts thereof, which have a selective $\beta_2$-adrenergic receptor stimulating effect with relieved burdens on the heart such as tachycardia.

BACKGROUND ART

As substituted phenylethanolaminotetralin derivatives, compounds having gut selective sympathomimetic and antipollakiuria activities have been disclosed, e.g., a compound represented by the general formula:

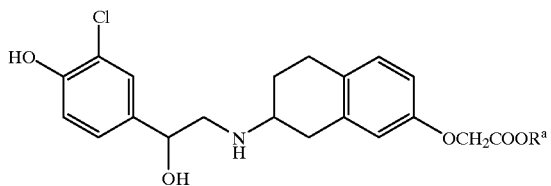

(wherein $R^a$ represents a hydrogen atom or an ethyl group), hydrochloride or oxalate thereof, or single optical isomers thereof; and a compound represented by the formula:

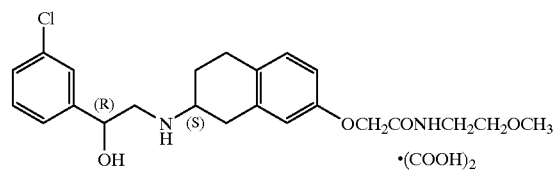

(wherein the carbon atom marked with (R) represents a carbon atom in R configuration; and the carbon atom marked with (S) represents a carbon atom in S configuration) (cf. a published Japanese patent application (kohyo) No. Hei 6-506676 and a published Japanese patent application (kohyo) No. Hei 6-506955).

However, these compounds are $\beta_3$-adrenergic receptor stimulating agents having a remarkable $\beta_3$-adrenergic receptor stimulating effect.

DISCLOSURE OF INVENTION

The present invention relates to 3,4-disubstituted phenylethanolaminotetralincarboxamide derivatives represented by the general formula:

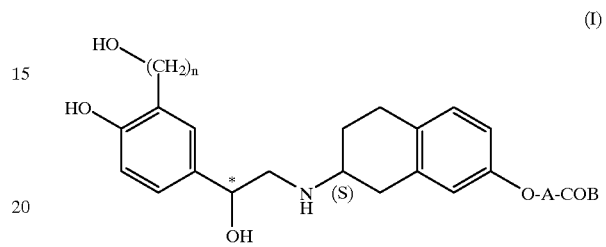

(wherein A represents a lower alkylene group; B represents an amino group, a di(lower alkyl)amino group or a 3 to 7-membered alicyclic amino group which may contain an oxygen atom in the ring; n is an integer of 1 or 2; the carbon atom marked with * represents a carbon atom in R configuration, S configuration or a mixture thereof; and the carbon atom marked with (S) represents a carbon atom in S configuration) and pharmaceutically acceptable salts thereof.

The present invention relates to a pharmaceutical composition comprising the above 3,4-disubstituted phenylethanolaminotetralincarboxamide derivative or pharmaceutically acceptable salt thereof.

The present invention relates to an agent for the prevention of threatened abortion and premature labor, a bronchodilator and an agent for pain remission and stone removal in urolithiasis which comprises as the active ingredient the above 3,4-disubstituted phenylethanolaminotetralincarboxamide derivative or pharmaceutically acceptable salt thereof.

The present invention relates to a method for the prevention of threatened abortion and premature labor, the prevention and treatment of diseases associated with bronchiostenosis and airway obstruction, and pain remission and stone removal in urolithiasis which comprises administering the above 3,4-disubstituted phenylethanolaminotetralincarboxamide derivative or pharmaceutically acceptable salt thereof.

The present invention relates to a use of the above 3,4-disubstituted phenylethanolaminotetralincarboxamide derivative or pharmaceutically acceptable salt thereof for the manufacture of a pharmaceutical composition for the prevention of threatened abortion and premature labor, the prevention and treatment of diseases associated with bronchiostenosis and airway obstruction, and pain remission and stone removal in urolithiasis.

Furthermore, the present invention relates to a use of the above 3,4-disubstituted phenylethanolaminotetralincarboxamide derivative or pharmaceutically acceptable salt thereof as an agent for the prevention of threatened abortion and premature labor, a bronchodilator and an agent for pain remission and stone removal in urolithiasis.

BEST MODE FOR CARRYING OUT THE INVENTION

In order to find an excellent $\beta_2$-adrenergic receptor stimulating agent, the inventors of the present invention made extensive studies and found that certain 3,4-disubstituted phenylethanolaminotetralincarboxamide derivatives represented by the above general formula (I) have a potent and selective $\beta_2$-adrenergic receptor stimulating effect and are remarkably useful as $\beta_2$-adrenergic receptor stimulating agents, thereby forming the basis of the present invention.

Accordingly, the present invention relates to 3,4-disubstituted phenylethanolaminotetralincarboxamide derivatives represented by the general formula:

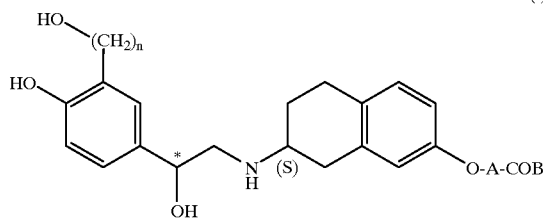

(I)

(wherein A represents a lower alkylene group; B represents an amino group, a di(lower alkyl)amino group or a 3 to 7-membered alicyclic amino group which may contain an oxygen atom in the ring; n is an integer of 1 or 2; the carbon atom marked with * represents a carbon atom in R configuration, S configuration or a mixture thereof; and the carbon atom marked with (S) represents a carbon atom in S configuration) and pharmaceutically acceptable salts thereof, which have a $\beta_2$-adrenergic receptor stimulating effect with higher selectivity in comparison with a $\beta_1$-adrenergic receptor stimulating effect and with relieved burdens on the heart such as tachycardia.

In the compounds represented by the above general formula (I) of the present invention, the term "di(lower alkyl)amino group" means an amino group di-substituted with straight or branched alkyl groups having 1 to 6 carbon atoms (e.g., methyl, ethyl, propyl, isopropyl), such as a dimethylamino group, a diethylamino group, an ethylmethylamino group and the like. Also, the term "lower alkylene group" means a straight alkylene group having 1 to 3 carbon atoms such as a methylene group, an ethylene group and a trimethylene group, and the term "3 to 7-membered alicyclic amino group which may contain an oxygen atom in the ring" means a 1-pyrrolidinyl group, a piperidino group, a morpholino group or the like.

The compounds represented by the above general formula (I) of the present invention can be prepared by the following procedures.

For example, the compounds of the above general formula (I) can be prepared by subjecting an amine compound represented by the general formula:

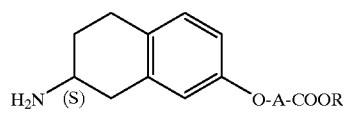

(II)

(wherein R is a lower alkyl group; and A and the carbon atom marked with (S) are as defined in the foregoing) to N-alkylation using an alkylating agent represented by the general formula:

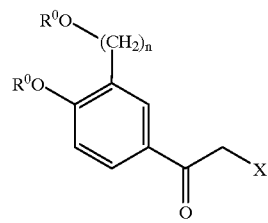

(III)

(wherein $R^0$ is a hydroxy-protective group; X is a halogen atom; and n is as defined in the foregoing), reducing the resulting compound in the usual way, removing the hydroxy-protective group as occasion demands to give a compound represented by the general formula:

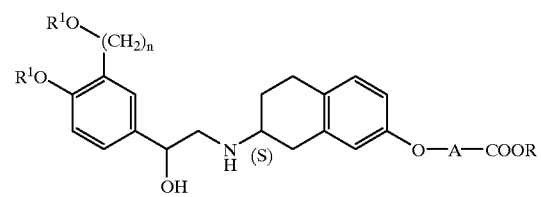

(IV)

(wherein $R^1$ is a hydrogen atom or a hydroxy-protective group; and A, R, n and the carbon atom marked with (S) are as defined in the foregoing), subjecting the resulting compound to amidation in the usual way using an amine compound represented by the general formula:

B—H (V)

(wherein B is as defined in the foregoing), and removing the hydroxy-protective group as occasion demands.

The compounds represented by the above general formula (I) of the present invention can be prepared by subjecting an amine compound represented by the general formula:

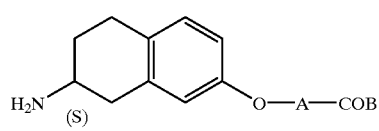

(VI)

(wherein A, B and the carbon atom marked with (S) are as defined in the foregoing) to N-alkylation using an alkylating agent represented by the above general formula (III), reducing the resulting compound in the usual way, and removing the hydroxy-protective group.

The compounds represented by the above general formula (I) of the present invention can be also prepared by allowing a mandelic acid derivative represented by the general formula:

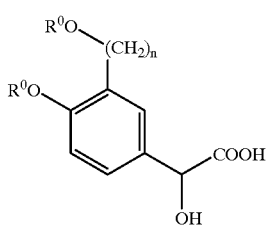

(VII)

(wherein R⁰ and n are as defined in the foregoing) to react with an amine compound represented by the formula:

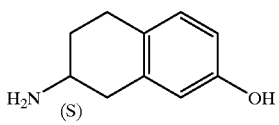

(VIII)

(wherein the carbon atom marked with (S) is as defined in the foregoing) in the presence of a condensing agent to give a compound represented by the general formula:

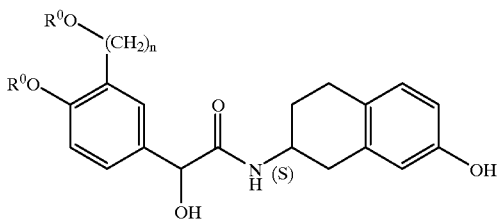

(IX)

(wherein R⁰, n and the carbon atom marked with (S) are as defined in the foregoing), reducing the resulting compound using a reagent such as borane-dimethylsulfide complex to prepare a compound represented by the general formula:

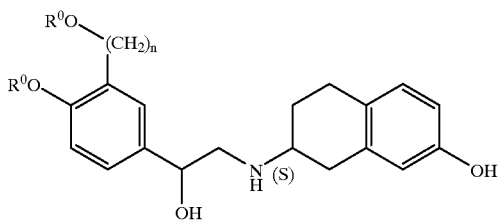

(X)

(wherein R⁰, n and the carbon atom marked with (S) are as defined in the foregoing), protecting the alcoholic hydroxy group and amino group with a reagent such as trifluoroacetic anhydride as occasion demands, subjecting the resulting compound to O-alkylation using an alkylating agent represented by the general formula:

X—A—COB    (XI)

(wherein A, B and X are as defined in the foregoing), and removing the protective group.

The amine compounds represented by the above general formula (II) which are used as starting materials in the aforementioned production process can be prepared by a process described in a literature or analogous processes thereto (for example, *Eur. J. Med. Chem.*, No. 29, pp. 259–267 (1994); a published Japanese patent application (Kokai) No. Hei 3-14548).

Among the alkylating agents represented by the above general formula (III) which are used as starting materials in the aforementioned production processes, compounds wherein n is 1 can be prepared, for example, by allowing a ketone compound represented by the formula:

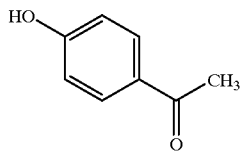

(XII)

to react with formalin in the presence of hydrochloric acid to prepare a compound represented by the formula:

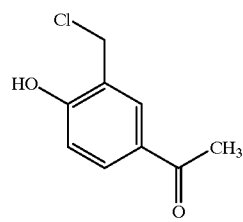

(XIII)

subjecting the resulting compound to acetylation and acetoxylation using acetic anhydride and sodium acetate to give a compound represented by the formula:

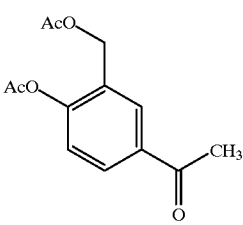

(XIV)

(wherein Ac represents an acetyl group), subjecting the resulting compound to halogenation in the usual way using a halogenating agent, subjecting the resulting halogeno compound (the corresponding bromo compound is described in *J. Med. Chem.*, No. 13, pp. 674–680 (1970)) represented by the general formula:

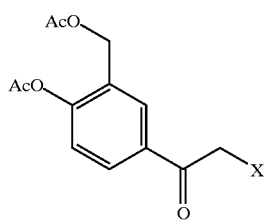

(XV)

(wherein Ac and X are as defined in the foregoing) to deacetylation in the usual way as occasion demands, and introducing a protective group to a hydroxy group using a reagent such as acetone dimethyl acetal.

Among the alkylating agents represented by the above general formula (III) which are used as starting materials in the aforementioned production processes, compounds wherein n is 2 can be prepared by protecting the hydroxy group of a phenylacetate derivative represented by the general formula:

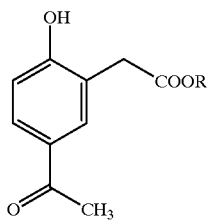

(XVI)

(wherein R is as defined in the foregoing) in the usual way using a reagent such as benzyl bromide, further protecting the carbonyl group using ethylene glycol and then reducing the derivative in the usual way using a reducing agent such as lithium aluminum hydride to convert it into an alcohol compound represented by the general formula:

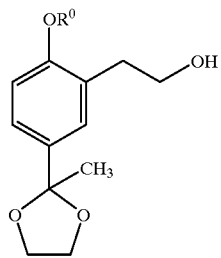

(XVII)

(wherein $R^0$ is as defined in the foregoing), protecting the hydroxy group of the resulting compound using a reagent such as benzyl bromide, removing the carbonyl-protective group to prepare a compound represented by the general formula:

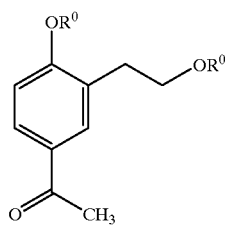

(XVIII)

(wherein $R^0$ is as defined in the foregoing), and then subjecting the resulting compound to halogenation in the usual way using a halogenating agent.

The amine compounds represented by the above general formula (VI) which are used as starting materials in the aforementioned production process can be prepared by subjecting a phenol compound represented by the general formula:

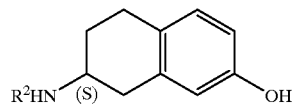

(XIX)

(wherein $R^2$ is an amino-protective group; and the carbon atom marked with (S) is as defined in the foregoing) to O-alkylation using an alkylating agent represented by the above general formula (XI) and then removing the amino-protective group, or by protecting the amino group of an amine compound represented by the above general formula (II) using an appropriate reagent, converting the resulting compound into a free carboxylic acid or reactive functional derivative thereof as occasion demands, subjecting the resulting compound to amidation using an amine compound represented by the above general formula (V) in the presence or absence of a condensing agent, and removing the amino-protective group.

Among the compounds represented by the above general formula (I) of the present invention, single isomers can be prepared, for example, by subjecting a diastereomer mixture obtained by the aforementioned processes to fractional recrystallization in the usual way, or by allowing an optically active mandelic acid derivative represented by the general formula:

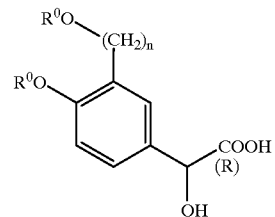

(XX)

(wherein the carbon atom marked with (R) is a carbon atom in R configuration; and $R^0$ and n are as defined in the foregoing) or another optically active mandelic acid derivative represented by the general formula:

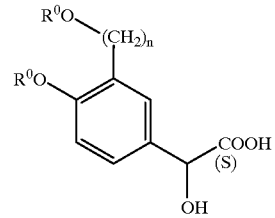

(XXI)

(wherein $R^0$, n and the carbon atom marked with (S) are as defined in the foregoing) to react with an amine compound represented by the above formula (VIII) in the presence of a condensing agent to give a single isomer represented by the general formula:

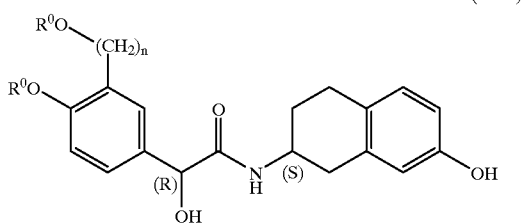

(XXII)

(wherein $R^0$, n, the carbon atom marked with (R) and the carbon atom marked with (S) are as defined in the foregoing) or another single isomer represented by the general formula:

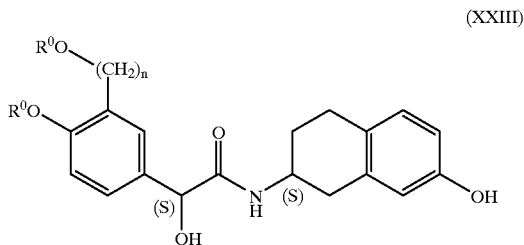

(XXIII)

(wherein $R^0$, n and the carbons atom marked with (S) are as defined in the foregoing), reducing the resulting single isomer using a reagent such as borane-dimethylsulfide complex to prepare a compound represented by the general formula:

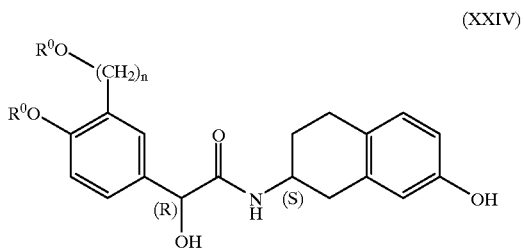

(XXIV)

(wherein $R^0$, n, the carbon atom marked with (R) and the carbon atom marked with (S) are as defined in the foregoing) or another compound represented by the general formula:

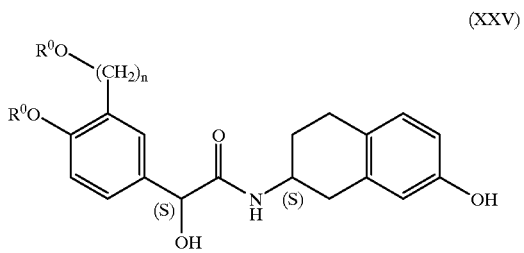

(XXV)

(wherein $R^0$, n and the carbon atoms marked with (S) are as defined in the foregoing), protecting the alcoholic hydroxy group and amino group using a reagent such as trifluoroacetic anhydride as occasion demands, subjecting the resulting compound to O-alkylation using an alkylating agent represented by the above general formula (XI), and removing the protective group.

Among the compounds represented by the above general formula (I) of the present invention, single isomers can be also prepared by subjecting a diastereomer mixture obtained as an intermediate in the aforementioned processes to column chromatography or fractional recrystallization to isolate the corresponding single isomer and then carrying out the same reaction using said single isomer.

The phenylacetate derivatives represented by the above general formula (XVI) which are used as starting materials in the aforementioned production process can be prepared by a process described in a literature or analogous processes thereto (for example, a published Japanese patent application (kohyo) No. Sho 61-500915, a published Japanese patent application (kokai) No. Sho 57-135049).

The optically active mandelic acid derivatives and mixtures thereof represented by the above general formulae (VII), (XX) and (XXI) which are used as starting materials in the aforementioned production process can be derived from the commercially available corresponding dihydroxy compounds or can be prepared by allowing a bromine compound represented by the general formula:

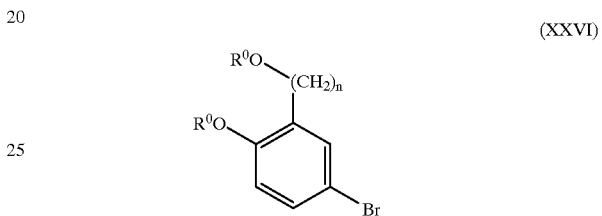

(XXVI)

(wherein $R^0$ and n are as defined in the foregoing), which can be obtained in accordance with a process described in a literature or analogous processes thereto, to react with diethyl oxalate, reducing the resulting phenylglyoxylic acid derivative using a reagent such as sodium borohydride, and hydrolyzing the ester compound to give a mandelic acid derivative represented by the above general formula (VII), and subjecting the derivative to optical resolution in the usual way using a resolving reagent such as optically active 1-(1-naphthyl)ethylamine as occasion demands.

The optically active mandelic acid derivatives and mixtures thereof represented by the above general formulae (VII), (XX) and (XXI) can be also prepared by subjecting a benzaldehyde derivative represented by the general formula:

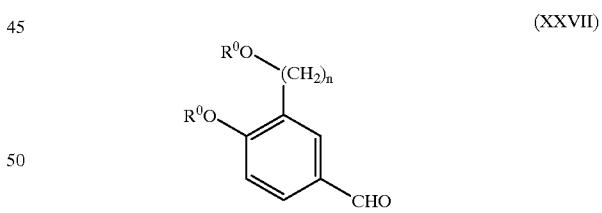

(XXVII)

(wherein $R^0$ and n are as defined in the foregoing) to cyanation, hydrolyzing the resulting cyano compound in the usual way, and subjecting the resulting compound to optical resolution in a similar manner to that described above.

The compounds of the present invention obtained by the aforementioned production processes can be easily isolated and purified by conventional separation means such as fractional recrystallization, purification using column chromatography, solvent extraction and the like.

The 3,4-disubstituted phenylethanolaminotetralincarboxamide derivative represented by the above general formula (I) of the present invention can be converted into its pharmaceutically acceptable salts in the usual way. Examples of such salts include acid addition salts with mineral acids (e.g., hydrochloric acid, hydrobromic acid, hydroiodic acid, sulfuric acid, nitric acid, phosphoric acid and the like), acid addition salts with organic acids (e.g., formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like) and salts with inorganic bases such as a sodium salt and a potassium salt. The resulting salts have the same pharmacological activities as those of the free forms.

In addition, the compounds represented by the above general formula (I) of the present invention also include hydrates thereof and solvates thereof with pharmaceutically acceptable solvents (e.g., ethanol).

The compounds represented by the above general formula (I) of the present invention exist in two isomer forms of R configuration and S configuration based on the asymmetric carbon atom having a hydroxy group. Either one of the isomers or a mixture thereof can be used in the present invention, and the R configuration isomer is desirable.

When the in vitro test for measuring $\beta_2$-adrenergic receptor stimulating activity was carried out in the usual way using isolated rat pregnant uterus, the compounds represented by the above general formula (I) of the present invention showed an activity to relax 50% of the spontaneous contractions of rat myometrium (i.e., $EC_{50}$) at an approximate mol concentration of $5.0 \times 10^{-10}$ to $5.0 \times 10^{-7}$. For example, 2[(2S)-2-[[(2RS)-2-hydroxy-2-(4-hydroxy-3-hydroxymethylphenyl)ethyl]amino]-1,2,3,4-tetrahydronaphthalen-7-yloxy]-N,N-dimethylacetamide showed the $EC_{50}$ value at a mol concentration of $5.3 \times 10^{-9}$, and 2-[(2S)-2-[[(2R)-2-hydroxy-2-(4-hydroxy-3hydroxymethylphenyl)ethyl]amino]-1,2,3,4-tetrahydronaphthalen-7-yloxy]-N,N-dimethylacetamide at a mol concentration of $2.6 \times 10^{-9}$. Thus, the compounds of the present invention have markedly potent $\beta_2$-adrenergic receptor stimulating effect and therefore are remarkably useful as $\beta_2$-adrenergic receptor stimulating agents.

When the in vitro test for measuring $\beta_1$-adrenergic receptor stimulating activity was carried out in the usual way using isolated rat atrium, the compounds represented by the above general formula (I) of the present invention showed an activity to increase 20 beats per minute of rat heart rate ($EC_{20}$ value) at an approximate mol concentration of $5.0 \times 10^{-7}$ or more. For example, 2-[(2S)-2-[[(2RS)-2-hydroxy-2-(4-hydroxy-3-hydroxymethylphenyl)ethyl]amino]-1,2,3,4-tetrahydronaphthalen-7-yloxy]-N,N-dimethylacetamide showed the $EC_{20}$ value at a mol concentration of $2.5 \times 10^{-6}$, and 2-[(2S)-2-[[(2R)-2-hydroxy-2-(4-hydroxy-3-hydroxymethylphenyl)ethyl]amino]-1,2,3,4-tetrahydronaphthalen-7-yloxy]-N,N-dimethylacetamide at a mol concentration of $9.4 \times 10^{-7}$. Thus, the compounds of the present invention have markedly weak $\beta_1$-adrenergic receptor stimulating effect in comparison with the aforementioned $\beta_2$-adrenergic receptor stimulating effect.

In consequence, the compounds of the present invention have markedly potent $\beta_2$-adrenergic receptor stimulating effect with markedly high selectivity in comparison with $\beta_1$-adrenergic receptor stimulating effect, so that these are a extremely useful and selective $\beta_2$-adrenergic receptor stimulating agents of in which burdens on the heart are reduced due to suppression of side effects upon the heart (e.g., tachycardia) caused by $\beta_1$-adrenergic receptor stimulating effect.

The present invention is a selective $\beta_2$-adrenergic receptor stimulating agent which is extremely useful as, for example, an agent for the prevention of threatened abortion, premature labor, a bronchodilator (an agent for the prevention and treatment of diseases associated with bronchiostenosis and airway obstruction) and an agent for pain remission or stone removal in urolithiasis.

Also, the compounds represented by the above general formula (I) of the present invention are extremely stable compounds and therefore have excellent storage stability.

When the 3,4-disubstituted phenylethanolaminotetralin-carboxamide derivatives represented by the above general formula (I) of the present invention and pharmaceutically acceptable salts thereof are used in the practical treatment, they are administered orally or parenterally in the form of appropriate pharmaceutical compositions such as tablets, powders, fine granules, granules, capsules, injections and the like. These pharmaceutical compositions can be formulated in accordance with conventional methods using conventional pharmaceutical carriers, excipients and other additives.

The dose is appropriately decided depending on the sex, age, body weight, degree of symptoms and the like of each patient to be treated, which is approximately within the range of from 1 to 1,000 mg per day per adult human in the case of oral administration and approximately within the range of from 0.01 to 100 mg per day per adult human in the case of parenteral administration, and the daily dose can be divided into one to several doses per day.

EXAMPLE

The contents of the present invention are described further in detail with reference to the following Reference Examples, Examples and Test Examples, but the present invention is not limited thereto. All melting points of the compounds described in Reference Examples and Examples were uncorrected.

Reference Example 1

(S)-4-(2-Amino-1,2,3,4-tetrahydronaphthalen-7-yloxy)-N, N-dimethylbutyramide (S)-2-(tert-Butoxycarbonylamino)-7-hydroxytetralin (400 mg) was dissolved in 8 ml of N,N-dimethylformamide, 3.16 g of cesium carbonate and 650 µl of ethyl 4-bromobutyrate were added to the solution, and the mixture was stirred at room temperature for 1.5 hours. After addition of water, the reaction mixture was extracted with ethyl acetate, and the extract was washed with water and then dried over anhydrous magnesium sulfate. The solvent was evaporated under reduced pressure and the residue was purified by silica gel medium pressure liquid column chromatography (eluent: hexane/ethyl acetate=1/1) to give 488 mg of ethyl (S)-4-[2-(tert-butoxycarbonylamino)-1,2,3,4-tetrahydronaphthalen-7-yloxy]butyrate having a meltin( point of 96 to 98° C.

IR (KBr): 3360, 1723, 1680 cm$^{-1}$; $^1$H-NMR (CDCl$_3$); δ ppm: 1.26 (3H, t, J=7.1 Hz), 1.45 (9H, s), 1.65–1.80 (1H, m), 2.00–2.15 (3H, m), 2.50 (2H, t, J=7.3 Hz), 2.59 (1H, dd, J=16.5, 7.9 Hz), 2.75–2.85 (2H, m), 3.07 (1H, dd, J=16.5, 4.6 Hz), 3.90–4.05 (3H, m), 4.14 (2H, q, J=7.1 Hz), 4.50–4.65 (1H, m), 6.58 (1H, d, J=2.6 Hz), 6.68 (1H, dd, J=8.4, 2.6 Hz), 6.99 (1H, d, J=8.4 Hz); Specific rotation: $[\alpha]_D^{25}$=−50.7° (c=1.03, MeOH)

Ethyl (S)-4-[2-(tert-butoxycarbonylamino)-1,2,3,4-tetrahydronaphthalen-7-yloxy]butyrate (988 mg) was dissolved in a mixture of 15 ml of ethanol and 15 ml of methanol, 3.0 ml of 2 N aqueous sodium hydroxide solution was added to the solution, and the mixture was stirred at room temperature for 2 hours. The reaction solution was concentrated under reduced pressure, 10% aqueous citric acid solution was added to the residue, and the mixture was extracted with ethyl acetate. The extract was washed with brine and dried over anhydrous magnesium sulfate. By evaporating the solvent under reduced pressure, 914 mg of (S)-4-[2-(tert-butoxycarbonylamino)1,2,3,4-tetrahydronaphthalen-7-yloxy]butyric acid having a melting point of 150 to 153° C. was obtained.

IR (KBr): 3452, 3365, 1691 cm$^{-1}$; $^1$H-NMR (CDCl$_3$); δ ppm: 1.45 (9H, s), 1.65–1.80 (1H, m), 2.00–2.20 (3H, m), 2.55–2.70 (3H, m), 2.75–2.85 (2H, m), 3.00–3.15 (1H, m), 3.90–4.10 (3H, m), 4.55–4.70 (1H, m), 6.58 (1H, d, J=2.6 Hz), 6.68 (1H, dd, J=8.4, 2.6 Hz), 6.99 (1H, d, J=8.4 Hz); Specific rotation: $[\alpha]_D^{25}$=−53.5° (c=0.52, MeOH)

(S)-4-[2-(tert-Butoxycarbonylamino)-1,2,3,4-tetrahydronaphthalen-7-yloxy]butyric acid (399 mg) was dissolved in 5 ml of tetrahydrofuran, 204 mg of N,N'-carbonyldiimidazole was added with stirring under ice-cooling, followed by 2 hours of reaction. Then, a solution of 1.40 g of dimethylamine in 2 ml of tetrahydrofuran was added with stirring under ice-cooling, and the mixture was subjected to 45 minutes of reaction and then to 45 minutes of reaction at room temperature. The reaction solution was concentrated under reduced pressure, water was added to the residue, and the mixture was extracted with diethyl ether. The extract was washed with 10% aqueous citric acid solution, water, saturated aqueous sodium bicarbonate solution and water in that order and then dried over anhydrous magnesium sulfate. By evaporating the solvent under reduced pressure, 396 mg of (S)4-[2-(tert-butoxycarbonylamino)-1,2,3,4-tetrahydronaphthalen-7-yloxy]-N,N-dimethylbutyramide having a melting point of 97 to 101° C. was obtained.

IR (KBr): 3325, 1709, 1624 cm$^{-1}$; $^1$H-NMR (CDCl$_3$); δ ppm: 1.45 (9H, s), 1.65–1.80 (1H, m), 2.00–2.15 (3H, m), 2.51 (2H, t, J=7.2 Hz), 2.59 (1H, dd, J=16.5, 8.1 Hz), 2.75–2.85 (2H, m), 2.95 (3H, s), 3.00–3.10 (4H, m), 3.90–4.00 (3H, m), 4.58 (1H, br s), 6.59 (1H, d, J=2.6 Hz), 6.69 (1H, dd, J=8.4, 2.6 Hz), 6.98 (1H, d, J=8.4 Hz); Specific rotation: $[\alpha]_D^{25}$=−50.0° (c=0.50, MeOH)

(S)-4-[2-(tert-Butoxycarbonylamino)-1,2,3,4-tetrahydronaphthalen-7-yloxy]-N,N-dimethylbutyramide (396 mg) was dissolved in 5 ml of methylene chloride, a solution of 5 ml of trifluoroacetic acid in 5 ml of methylene chloride was added to the solution with stirring under ice-cooling, and the mixture was stirred for 15 minutes and then subjected to 15 minutes of reaction at room temperature. The reaction solution was concentrated under reduced pressure, methylene chloride, water and sodium bicarbonate were added to the residue, and the mixture was stirred at room temperature for 30 minutes. The organic layer was separated and dried over anhydrous magnesium sulfate. By evaporating the solvent under reduced pressure, 263 mg of (S)-4-(2-amino-1,2,3,4-tetrahydronaphthalen-7-yloxy)-N,N-dimethylbutyramide was obtained in an oily form.

IR (neat): 3404, 1618 cm$^{-1}$; $^1$H-NMR (CDCl$_3$); δ ppm: 1.75–1.90 (1H, m), 2.00–2.25 (3H, m), 2.45–2.55 (2H, m), 2.65–2.90 (3H, m), 2.94 (3H, s), 3.00 (3H, s), 3.05–3.20 (1H, m), 3.30–3.50 (1H, m), 3.96 (2H, t, J=5.9 Hz), 5.89 (2H, br s), 6.60 (1H, d, J=2.3 Hz), 6.68 (1H, dd, J=8.4, 2.3 Hz), 6.96 (1H, d, J=8.4 Hz); Specific rotation: $[\alpha]_D^{25}$=−46.2° (c=0.45, MeOH)

Reference Example 2
(S)-2-(2-Amino-1,2,3,4-tetrahydronaphthalen-7-yloxy)-N,N-dimethylacetamide acetate (S)-2-(Benzyloxycarbonylamino)-7-hydroxytetralin (13.4 g) was dissolved in 120 ml of N,N-dimethylformamide, 8.27 g of 2-bromo-N,N-dimethylacetamide and 22.0 g of cesium carbonate were added to the solution, and the mixture was stirred at room temperature for 6 hours. The reaction solution was poured into ice-water, the mixture was extracted with ethyl acetate, and the extract was washed with water and then dried over anhydrous magnesium sulfate. The solvent was evaporated under reduced pressure and the resulting residue was crystallized by adding diethyl ether to give 14.0 g of (S)-2-[2-(benzyloxycarbonylamino)-1,2,3,4-tetrahydronaphthalen-7-yloxy]-N,N-dimethylacetamide having a melting point of 117 to 118° C.

IR (KBr): 3465, 3284, 1704, 1667 cm$^{-1}$; $^1$H-NMR (CDCl$_3$); δ ppm: 1.70–1.85 (1H, m), 2.00–2.10 (1H, m), 2.63 (1H, dd, J=16.5, 7.4 Hz), 2.75–2.85 (2H, m), 2.97 (3H, s), 3.05–3.15 (4H, m), 4.00–4.10 (1H, m), 4.64 (2H, s), 4.75–4.85 (1H, m), 5.10 (2H, s), 6.63 (1H, d, J=2.7 Hz), 6.75 (1H, dd, J=8.4, 2.7 Hz), 6.99 (1H, d, J=8.4 Hz), 7.25–7.40 (5H, m); Specific rotation: $[\alpha]_D^{25}$=−41.0° (c=1.02, MeOH)

(S)-2-[2-(Benzyloxycarbonylamino)-1,2,3,4-tetrahydronaphthalen-7-yloxy]-N,N-dimethylacetamide (100 mg) and 20 mg of 10% palladium-carbon were suspended in 5 ml of acetic acid and the suspension was stirred at room temperature for 3 hours in an atmosphere of hydrogen. The catalyst was removed by filtration, the filtrate was concentrated under reduced pressure, and the residue was recrystallized from ethanoldiethyl ether to give 72 mg of (S)-2-(2-amino-1,2,3,4-tetrahydronaphthalen-7-yloxy)-N,N-dimethylacetamide acetate having a melting point of 135 to 142° C.

IR (KBr): 3431, 2636, 2158, 1656 cm$^{-1}$; $^1$H-NMR (DMSO-d$_6$); δ ppm: 1.40–1.60 (1H, m), 1.81 (3H, s), 1.85–2.00 (1H, m), 2.40–2.55 (1H, m), 2.60–3.15 (10H, m), 4.71 (2H, s), 5.60–6.55 (3H, m), 6.61 (1H, d, J=2.7 Hz), 6.65 (1H, dd, J=8.4, 2.7 Hz), 6.95 (1H, d, J=8.4 Hz); Specific rotation: $[\alpha]_D^{25}$=−46.8° (c=0.99, AcOH)

Reference Example 3
2-Bromo-1-(2,2-dimethylbenzo[1,2-d]-1,3-dioxan-6-yl)-1-ethanone 2-Acetoxymethyl-4-bromoacetylphenyl acetate (18.6 g) was dissolved in 90 ml of methanol, 100 ml of 47% hydrobromic acid was added with stirring under ice-cooling, and the mixture was subjected to 16 hours of reaction at room temperature. Water was added to the reaction solution with stirring under ice-cooling, and the resulting precipitates were collected by filtration and washed with water and hexane to give 9.54 g of 2-bromo-4'-hydroxy-3'-hydroxymethylacetophenone having a melting point of 117 to 119° C.

IR (KBr): 3440, 1677 cm$^{-1}$; $^1$H-NMR (DMSO-d$_6$); δ ppm: 4.50 (2H, s), 4.75 (2H, s), 5.10 (1H, br s), 6.87 (1H, d, J=8.5 Hz), 7.79 (1H, dd, J=8.5, 2.4 Hz), 7.99 (1H, d, J=2.4 Hz), 10.52 (1H, s)

2-Bromo-4'-hydroxy-3'-hydroxymethylacetophenone (17.7 g), 124 mg of p-toluenesulfonic acid monohydrate and 256 ml of acetone dimethyl acetal were dissolved in 256 ml of acetone and the mixture was heated under reflux for 30 minutes. After cooling, an aqueous saturated sodium bicarbonate solution was added to the reaction solution, and the mixture was extracted with ethyl acetate. The extract was washed with water and brine and then dried over anhydrous magnesium sulfate. The solvent was evaporated under reduced pressure and the resulting residue was purified by silica gel medium pressure liquid column chromatography (eluent: hexane/ethyl acetate=7/1) to give 11.9 g of 2-bromo-1-(2,2-dimethylbenzo[1,2-d]-1,3-dioxan-6-yl)-1-ethanone having a melting point of 52 to 54° C.

IR (KBr): 1693 cm$^{-1}$; $^1$H-NMR (CDCl$_3$); δ ppm: 1.57 (6H, s), 4.37 (2H, S), 4.89 (2H, s), 6.88 (1H, d, J=8.6 Hz), 7.69 (1H, d, J=2.2 Hz), 7.82 (1H, dd, J=8.6, 2.2 Hz)

Reference Example 4

(−)-2-[(2S)-2-[[(2R)-2-(2,2-Dimethylbenzo[1,2-d]-1,3-dioxan-6yl)-2-hydroxyethyl]amino]-1,2,3,4-tetrahydronaphthalen-7-yloxy)-N,N-dimethyacetamide 6-Bromo-2,2-dimethylbenzo[1,2-d]-1,3-dioxane (30.0 g) was dissolved in 610 ml of tetrahydrofuran, 136 ml of 1.56 M n-butyl lithium in hexane was added to the solution with stirring at −80° C., and the mixture was subjected to 15 minutes of reaction. With stirring at −80° C., the reaction solution was added to a solution of 21.6 g of diethyl oxalate in 200 ml of tetrahydrofuran, and the mixture was subjected to 1 hour of reaction. Then, 100 ml of ethanol and a solution of 1.40 g of sodium borohydride in 100 ml of ethanol were added in that order. The reaction solution was stirred at −30° C. for 30 minutes, 8.26 ml of acetic acid was added, and the mixture was stirred for 5 minutes. Then, a solution of 14.8 g of potassium bicarbonate in 50 ml of water was added, and the reaction solution was concentrated under reduced pressure. Water was added to the residue, and the mixture was extracted with ethyl acetate. The extract was washed with brine and then dried over anhydrous magnesium sulfate. The solvent was evaporated under reduced pressure and the resulting residue was purified by silica gel medium pressure liquid column chromatography (eluent: hexane/ethyl acetate=5/1) to give 25.1 g of ethyl 2-(2,2-dimethylbenzo[1,2-d]-1,3-dioxan-6-yl)2-hydroxyacetate in an oily form.

IR (neat): 3467, 1736 cm$^{-1}$; $^1$H-NMR (CDCl$_3$); δ ppm: 1.24 (3H, t, J=7.1 Hz), 1.54 (6H, s), 3.39 (1H, d, J=5.6 Hz), 4.10–4.35 (2H, m), 4.84 (2H, s), 5.06 (1H, d, J=5.6 Hz), 6.80 (1H, d, J=8.4 Hz), 7.03 (1H, d, J=1.9 Hz), 7.19 (1H, dd, J=8.4, 1.9 Hz)

Ethyl 2-(2,2-dimethylbenzo[1,2-d]-1,3-dioxan-6-yl)-2-hydroxyacetate (78.3 g) was dissolved in 145 ml of ethanol, 176 ml of 2 N aqueous sodium hydroxide solution was added to the solution with stirring under ice-cooling, and the mixture was subjected to 1.5 hours of reaction at room temperature. With stirring under ice-cooling, 174 ml of 2 N aqueous sulfuric acid solution was added to the reaction solution, water and brine were then added, and the mixture was extracted with ethyl acetate. The extract was washed with brine and then dried over anhydrous magnesium sulfate. The solvent was evaporated under reduced pressure and the resulting residue was dissolved in 210 ml of ethanol. Then, 50.3 g of (R)-(+)-1(1-naphthyl)ethylamine was added and the mixture was allowed to stand at room temperature to give 48.3 g of precipitated crystals. By recrystallizing the resulting crystals from 88 ml of ethanol, 43.6 g of 1:1:1 salt of (−)-(R)-2-(2,2-dimethylbenzo[1,2-d]-1,3-dioxan-6-yl)-2-hydroxyacetic acid, (R)-(+)-1-(1-naphthyl)ethylamine and ethanol having a melting point of 164 to 165° C. was obtained.

IR (KBr): 3327, 1567 cm$^{-1}$; $^1$H-NMR (CDCl$_3$); δ ppm: 1.15–1.30 (9H, m), 1.38 (3H, s), 3.70 (2H, q, J=7.0 Hz), 4.15 (1H, s), 4.38 (1H, d, J=15.2 Hz), 4.49 (1H, d, J=15.2 Hz), 4.71 (1H, q, J=6.7 Hz), 6.46 (1H, d, J=8.4 Hz), 6.53 (1H, d, J=1.8 Hz), 6.61 (1H, dd, J=8.4, 1.8 Hz), 7.30–7.45 (2H, m), 7.50–7.65 (2H, m), 7.75 (1H, d, J=8.4 Hz), 7.84 (1H, d, J=7.9 Hz), 7.91 (1H, d, J=8.1 Hz) Specific rotation: $[\alpha]_D^{25}$=−33.7° (c=0.52, MeOH)

A 1:1:1 salt (43.6 g) of (−)-(R)-2-(2,2-dimethylbenzo-[1,2-d]-1,3-dioxan-6-yl)-2-hydroxyacetic acid, (R)-(+)-1-(1-naphthyl)ethylamine and ethanol was suspended in a two layer mixture of 200 ml of water and 300 ml of ethyl acetate, 47.9 ml of 2 N aqueous sulfuric acid solution was added to the suspension with stirring under ice-cooling, and the mixture was stirred for 30 minutes. The reaction solution was filtered through Celite®, and the organic layer of the filtrate was washed with water and dried over anhydrous magnesium sulfate. The solvent was evaporated under reduced pressure and the resulting residue was recrystallized from ethyl acetatediisopropyl ether to give 22.8 g of (−)-(R)-2-(2,2-dimethylbenzo[1,2-d]-1,3-dioxan-6-yl)-2-hydroxyacetic acid having a melting point of 115 to 118° C. (decomposition).

IR (KBr): 3397, 2638, 1701 cm$^{-1}$; $^1$H-NMR (DMSO-d$_6$); δ ppm: 1.45 (6H, s), 4.81 (2H, s), 4.92 (1H, s), 5.80 (1H, br), 6.75 (1H, d, J=8.4 Hz), 7.09 (1H, d, J=1.8 Hz), 7.18 (1H, dd, J=8.4, 1.8 Hz), 12.50 (1H, br); Specific rotation: $[\alpha]_D^{25}$=−113.3° (c=1.54, MeCN)

(−)-(R)-2-(2,2-Dimethylbenzo[1,2-d]-1,3-dioxan-6-yl)2-hydroxyacetic acid (130 mg), 148 mg of (S)-2-amino-7-hydroxytetralin hydrobromide and 243 mg of benzotriazol-1-yloxytris(dimethylamino)phosphonium hexafluorophosphate were dissolved in 1.4 ml of N,N-dimethylformamide, 0.15 ml of triethylamine was added to the solution with stirring under ice-cooling, and the mixture was subjected to 15 hours of reaction. Water was added to the reaction solution and the mixture was extracted with ethyl acetate. The extract was washed with water and dried over anhydrous magnesium sulfate. The solvent was evaporated under reduced pressure and the resulting residue was purified by aminopropylated silica gel medium pressure liquid column chromatography (eluent: ethyl acetate/acetone=4/1) and then recrystallized from ethyl acetate to give 186 mg of (−)-(2R)-2-(2,2-dimethylbenzo[1,2-d]-1,3-dioxan-6-yl)-2-hydroxy-N-((2S)-7-hydroxy-1,2,3,4-tetrahydronaphthalen-2-yl)acetamide having a melting point of 169 to 170° C.

IR (KBr): 3373, 3263, 1642 cm$^{-1}$; $^1$H-NMR (CDCl$_3$); δ ppm: 1.49 (3H, S), 1.51 (3H, s), 1.60–1.80 (1H, m), 1.90–2.00 (1H, m), 2.50 (1H, dd, J=16.3, 8.3 Hz), 2.60–2.80 (2H, m), 2.92 (1H, dd, J=16.3, 5.0 Hz), 3.60 (1H, br), 4.15–4.25 (1H, m), 4.73 (2H, s), 4.93 (1H, s), 6.20 (1H, br), 6.36 (1H, d, J=2.5 Hz), 6.50 (1H, d, J=8.0 Hz), 6.59 (1H, dd, J=8.3, 2.5 Hz), 6.77 (1H, d, J=8.4 Hz), 6.88 (1H, d, J=8.3 Hz), 6.93 (1H, d, J=2.0 Hz), 7.12 (1H, dd, J=8.4, 2.0 Hz) Specific rotation: $[\alpha]_D^{25}$=−101.2° (c=0.52, MeOH)

(−)-(2R)-2-(2,2-Dimethylbenzo[1,2-d]-1,3-dioxan-6-yl)-2-hydroxy-N-((2S)-7-hydroxy-1,2,3,4-tetrahydronaphthalen-2-yl)acetamide (686 mg) was dissolved in 50 ml of tetrahydrofuran, 3.58 ml of 2 M borane-dimethylsulfide complex in tetrahydrofuran was added, and the mixture was heated under reflux for 3 hours. Then, a solution of 1.34 g of triethanolamine in 5.0 ml of tetrahydrofuran was added, and the mixture was again heated under reflux for 15 hours. After cooling, water was added to the reaction solution, and the mixture was extracted with ethyl acetate. The extract was washed with water and then dried over anhydrous magnesium sulfate. The solvent was evaporated under reduced pressure and the resulting residue was recrystallized from ethyl acetate to give 560 mg of (−)-(1R)-1-(2,2-dimethylbenzo[1,2-d]-1,3-dioxan-6-yl)-2-[((2S)-7-hydroxy-1,2,3,4-tetrahydronaphthalen-2-yl)amino]ethanol having a melting point of 156 to 158° C.

IR (KBr): 3400 cm$^{-1}$; $^1$H-NMR (CDCl$_3$); δ ppm: 1.50–1.70 (7H, m), 2.00–2.10 (1H, m), 2.55 (1H, dd, J=17.5, 10.4 Hz), 2.65–2.85 (3H, m), 2.90–3.10 (3H, m), 4.61 (1H, dd, J=9.1, 3.5 Hz), 4.84 (2H, s), 6.53 (1H, d, J=2.3 Hz), 6.60 (1H, dd, J=8.2, 2.3 Hz), 6.80 (1H, d, J=8.4 Hz), 6.94 (1H, d, J=8.2 Hz), 7.02 (1H, s), 7.14 (1H, d, J=8.4 Hz); Specific rotation: $[\alpha]_D^{25}$=−59.0° (c=1.02, MeOH)

(−)-(1R)-1-(2,2-Dimethylbenzo[1,2-d]-1,3-dioxan-6-yl) 2-[((2S)-7-hydroxy-1,2,3,4-tetrahydronaphthalen-2-yl) amino]-ethanol (5.15 g) and 11.3 ml of N,N- diisopropylethylamine were added to 125 ml of methylene chloride, a solution of 5.51 ml of trifluoroacetic anhydride in 16 ml of methylene chloride was added to the resulting suspension with stirring at −15° C., and the mixture was subjected to 30 minutes of reaction. The reaction solution was washed with water and dried over anhydrous magnesium sulfate. Then, the solvent was evaporated under reduced pressure. The resulting residue was dissolved in 63 ml of N,N-dimethylformamide, 5.0 g of molecular sieves 4A powder, 3.24 g of 2-bromo-N,N-dimethyl-acetamide and 19.0 g of cesium carbonate were added to the solution, and the mixture was stirred at room temperature for 2 hours. Then, 2.02 ml of diethylamine was added and the mixture was subjected to 20 minutes of reaction at room temperature. After adding 90 ml of water and 180 ml of methanol to the reaction solution under ice-cooling, the mixture was stirred at room temperature for 1.5 hours. Then, brine was added and the mixture was extracted with ethyl acetate. The extract was washed with brine and then dried over anhydrous magnesium sulfate. The solvent was evaporated under reduced pressure and the resulting residue was purified by aminopropylated silica gel medium pressure liquid column chromatography (eluent: ethyl acetate) to give 3.22 g of (−)-(2R)-2-[(2S)-2-[[2-(2,2-dimethylbenzo[1,2-d]-1,3-dioxan-6-yl)-2-hydroxyethyl]amino]-1,2,3,4-tetrahydronaphthalen-7-yloxy]-N,N-dimethylacetamide in an oily form.

IR (neat): 3401, 1656 cm$^{-1}$; $^1$H-NMR (CDCl$_3$); δ ppm: 1.50–1.70 (7H, m), 2.00–2.10 (1H, m), 2.56 (1H, dd, J=15.2, 8.0 Hz), 2.65–3.10 (12H, m), 4.59 (1H, dd, J=9.1, 3.5 Hz), 4.64 (2H, s), 4.84 (2H, s), 6.65 (1H, d, J=2.6 Hz), 6.73 (1H, dd, J=8.4, 2.6 Hz), 6.79 (1H, d, J=8.4 Hz), 6.99 (1H, d, J=8.4 Hz), 7.02 (1H, d, J=2.0 Hz), 7.14 (1H, dd, J=8.4, 2.0 Hz); Specific rotation: [α]$_D^{25}$=−46.0° (c=1.23, MeOH)

Reference Example 5

(−)-1-[2-[(2S)-2 -[[(2R)-2-(2,2-Dimethylbenzo[1,2-d]-1,3dioxan-6-yl)-2-hydroxyethyl]amino]-1,2,3,4-tetrahydronaphthalen-7-yloxy]acetyl]pyrrolidine The reactions and treatments of Reference Example 4 were repeated except that 1-bromoacetylpyrrolidine was used instead of 2-bromo-N,N-dimethylacetamide, thereby obtaining amorphous (−)-1-[2-[(2S)-2-[[(2R)-2-(2,2-dimethylbenzo[1,2-d]-1,3-dioxan-6-yl)-2-hydroxyethyl] amino]-1,2,3,4-tetrahydronaphthalen-7-yloxy]acetyl] pyrrolidine.

IR (film): 3401, 1649 cm$^{-1}$; $^1$H-NMR (CDCl$_3$); δ ppm: 1.45–1.70 (7H, m), 1.80–2.10 (5H, m), 2.56 (1H, dd, J=15.4, 8.3 Hz), 2.70–3.05 (6H, m), 3.45–3.60 (4H, m), 4.55–4.65 (3H, m), 4.85 (2H, s), 6.65 (1H, d, J=2.7 Hz), 6.73 (1H, dd, J=8.4, 2.7 Hz), 6.79 (1H, d, J=8.4 Hz), 6.99 (1H, d, J=8.4 Hz), 7.02 (1H, d, J=1.9 Hz), 7.14 (1H, dd, J=8.4, 1.9 Hz) Specific rotation: [α]$_D^{25}$=−47.0° (c=1.13, MeOH)

(−)-1-[2-[(2S)-2-[[(2R)-2-(2,2-Dimethylbenzo[1,2-d]-1, 3dioxan-6-yl)-2-hydroxyethyl]amino]-1,2,3,4-tetrahydronaphthalen-7-yloxy]acetyl]piperidine The reactions and treatments of Reference Example 4 were repeated except that 1-bromoacetylpiperidine was used instead of 2-bromo-N,N-dimethylacetamide, thereby obtaining amorphous (−)-1-[2-[(2S)-2-[[(2R)-2-(2,2-dimethylbenzo[1,2-d]1,3-dioxan-6-yl)-2-hydroxyethyl] amino]-1,2,3,4-tetrahydronaphthalen-7-yloxy]acetyl] piperidine.

IR (film): 3402, 1649 cm$^{-1}$ $^1$H-NMR (CDCl$_3$); δ ppm: 1.40–1.70 (13H, m), 1.95–2.10 (1H, m), 2.50–3.10 (7H, m), 3.40–3.60 (4H, m), 4.55–4.65 (3H, m), 4.85 (2H, s), 6.65 (1H, d, J=2.7 Hz), 6.73 (1H, dd, J=8.4, 2.7 Hz), 6.80 (1H, d, J=8.4 Hz), 6.99 (1H, d, J=8.4 Hz), 7.02 (1H, d, J=1.8 Hz), 7.14 (1H, dd, J=8.4, 1.8 Hz); Specific rotation: [α]$_D^{25}$=−45.6° (c=1.00, MeOH)

(−)-4-[2-[(2S)-2-[[(2R)-2-(2,2-Dimethylbenzo[1,2-d]-1, 3dioxan-6-yl)-2-hydroxyethyl]amino]-1,2,3,4-tetrahydronaphthalen-7-ylcxy]acetyl]morpholine The reactions and treatments of Reference Example 4 were repeated except that 4-bromoacetylmorpholine was used instead of 2-bromo-N,N-dimethylacetamide, thereby obtaining amorphous (−)-4-[2-[(2S)-2-[[(2R)-2-(2,2-dimethylbenzo[1,2-d]1,3-dioxan-6yl)-2-hydroxyethyl] amino]-1,2,3,4-tetrahydronaphthalen-7-yloxy]acetyl] morpholine.

IR (KBr): 3438, 1652 cm$^{-1}$; $^1$H-NMR (CDCl$_3$); δ ppm: 1.45–1.70 (7H, m), 2.00–2.10 (1H, m), 2.50–3.10 (7H, m), 3.55–3.75 (8H, m), 4.59 (1H, dd, J=9.1, 3.4 Hz), 4.65 (2H, s), 4.85 (2H, s), 6.65 (1H, d, J=2.6 Hz), 6.72 (1H, dd, J=8.4, 2.6 Hz), 6.80 (1H, d, J=8.4 Hz), 7.00 (1H, d, J=8.4 Hz), 7.03 (1H, d, J=1.8 Hz), 7.14 (1H, dd, J=8.4, 1.8 Hz) Specific rotation: [α]$_D^{25}$=−52.2° (c=0.54, MeOH)

Reference Example 6

The reactions of Reference Example 4 were repeated except that (S)-(−)-1-(1-naphthyl)ethylamine was used instead of (R)-(+)-1-(1-naphthyl)ethylamine to give (+)-(S)-2-(2,2dimethylbenzo[1,2-d]-1,3-dioxan-6-yl)-2-hydroxyacetic acid, and the following compounds were subsequently obtained.

(−)-2-[(2S)-2-[[(2S)-2-(2,2-Dimethylbenzo[1,2-d]-1,3-dioxan-6yl)-2-hydroxyethyl]amino]-1,2,3,4-tetrahydronaphthalen-7-yloxy]-N,N-dimethylacetamide Melting point: 130–131° C. (recrystallization solvent: ethyl acetate); IR (KBr): 3432, 1652 cm$^{-1}$; $^1$H-NMR (CDCl$_3$); δ ppm: 1.45–1.65 (7H, m), 2.00–2.10 (1H, m), 2.58 (1H, dd, J=16.0, 8.9 Hz), 2.65–3.10 (12H, m), 3.65 (1H, br), 4.60 (1H, dd, J=9.2, 3.5 Hz), 4.64 (2H, s), 4.85 (2H, s), 6.65 (1H, d, J=2.6 Hz), 6.73 (1H, dd, J=8.4, 2.6 Hz), 6.80 (1H, d, J=8.4 Hz), 6.99 (1H, d, J=8.4 Hz), 7.02 (1H, d, J=1.9 Hz), 7.14 (1H, dd, J=8.4, 1.9 Hz); Specific rotation: [α]$_D^{25}$=−25.6° (c=1.20, MeOH)

(−)-1-[2-[(2S)-2-[[(2S)-2-(2,2-Dimethylbenzo[1,2-d]-1,3-dioxan-6-yl)-2-hydroxyethyl]amino]-1,2,3,4-tetrahydronaphthalen-7-yloxy]acetyl]pyrrolidine Amorphous IR (KBr): 3415, 1649 cm$^{-1}$; $^1$H-NMR (CDCl$_3$); δ ppm: 1.50–1.70 (7H, m), 1.80–2.10 (5H, m), 2.55–3.10 (7H, m), 3.52 (4H, t, J=6.6 Hz), 4.55–4.65 (1H, m), 4.58 (2H, s), 4.85 (2H, s), 6.65 (1H, d, J=2.6 Hz), 6.74 (1H, dd, J=8.4, 2.7 Hz), 6.80 (1H, d, J=8.4 Hz), 6.95–7.05 (2H, m), 7.10–7.15 (1H, m) Specific rotation: [α]$_D^{25}$=−26.9° (c=1.00, MeOH)

Reference Example 7

2-[(2S)-2-[[(2RS)-2-[4-Benzyloxy-3-(2-benzyloxyethyl) phenyl]-2-hydroxyethyl]amino]-1,2,3,4-tetrahydronaphthalen-7-yloxyl]-N,N-dimethylacetamide Methyl 2-(5-acetyl-2-hydroxyphenyl)acetate (8.0 g) was dissolved in 120 ml of N,N-dimethylformamide, 5 ml of benzyl bromide and 5.8 g of potassium carbonate were added to the solution, and the mixture was stirred at room temperature for 16 hours. About 100 g of ice and 200 ml of hexane were added to the reaction solution, and the mixture was vigorously stirred while adding 200 ml of water. Thereafter, the precipitated crystals were collected by filtration and recrystallized from methylene chloride-hexane to give 10.1 g of methyl 2-(5-acetyl-2-benzyloxyphenyl) acetate having a melting point of 85 to 87° C.

IR (KBr): 1747, 1682 cm$^{-1}$; $^1$H-NMR (CDCl$_3$); δ ppm: 2.55 (3H, s), 3.64 (3H, s), 3.71 (2H, s), 5.16 (2H, s), 6.96

(1H, d, J=8.6 Hz), 7.30–7.40 (5H, m), 7.85 (1H, d, J=2.3 Hz), 7.89 (1H, dd, J=8.6, 2.3 Hz)

Methyl 2-(5-acetyl-2-benzyloxyphenyl)acetate (9.0 g), 18 ml of methyl orthoformate and 18 ml of ethylene glycol were dissolved in 300 ml of methylene chloride, 60 mg of p-toluenesulfonic acid monohydrate was added to the solution, and the mixture was heated under reflux for 12 hours. After cooling, 0.14 ml of triethylamine was added to the reaction solution and the mixture was stirred for 15 minutes. The reaction solution was partially purified by silica gel flash column chromatography (eluent: methylene chloride) and then further purified by silica gel medium pressure liquid column chromatography (eluent: hexane/diethyl ether=3/2) to give 9.2 g of methyl 2-[2-benzyloxy-5-(2-methyl-1,3-dioxolan-2-yl)phenyl]acetate in an oily form.

IR (neat); 1742 cm$^{-1}$; $^1$H-NMR (CDCl$_3$); δ ppm: 1.65 (3H, s), 3.63 (3H, s), 3.68 (2H, s), 3.80–3.85 (2H, m), 4.00–4.05 (2H, m), 5.07 (2H, s), 6.88 (1H, d, J=8.4 Hz), 7.30–7.45 (7H, m)

Methyl 2-[2-benzyloxy-5-(2-methyl-1,3-dioxolan-2-yl)phenyl]acetate (9.0 g) was dissolved in 130 ml of diethyl ether, 1.0 g of lithium aluminum hydride in small portions was added to the solution with stirring under ice-cooling, and the mixture was subjected to 1 hour of reaction. Water was added in small portions to the reaction solution with stirring under ice-cooling, and the formed precipitates were removed by filtration. By concentrating the resulting filtrate under reduced pressure, 9.0 g of 2-[2-benzyloxy-5-(2-methyl-1,3-dioxolan-2-yl)phenyl]ethanol was obtained in an oily form.

IR (neat): 3442 cm$^{-1}$; $^1$H-NMR (CDCl$_3$); δ ppm: 1.60–1.70 (4H, m) 2.96 (2H, t, J=6.5 Hz), 3.75–3.90 (4H, m), 3.95–4.10 (2H, m), 5.08 (2H, s), 6.89 (1H, dd, J=7.0, 2.0 Hz), 7.30–7.45 (7H, m) 2-[2-Benzyloxy-5-(2-methyl-1,3-dioxolan-2-yl)phenyl]-ethanol (9.0 g) was dissolved in 100 ml of N,N-dimethylformamide, 1.26 g of sodium hydride in 60% oil was added to the solution with stirring under ice-cooling, and the mixture was subjected to 1 hour of reaction at room temperature. Then, 3.75 ml of benzyl bromide was added with stirring under ice-cooling and the mixture was subjected to 16 hours of reaction at room temperature. Then, 100 g of ice and 100 ml of water were added to the reaction solution, the mixture was extracted with diethyl ether, and then the solvent was evaporated under reduced pressure. The resulting residue was dissolved in 50 ml of 1,2-dimethoxyethane, 10 ml of 1 N hydrochloric acid was added to the solution, and the mixture was stirred at room temperature for 30 minutes. Water was added, the mixture was extracted with diethyl ether, and the extract was dried over anhydrous magnesium sulfate. The solvent was evaporated under reduced pressure and the resulting residue was purified by silica gel medium pressure liquid column chromatography (eluent: hexane/diethyl ether=2/1) to give 8.5 g of 4-benzyloxy-3'-(2-benzyloxyethyl)acetophenone in an oily form.

IR (neat): 1677 cm$^{-1}$; $^1$H-NMR (CDCl$_3$); δ ppm: 2.54 (3H, s), 3.05 (2H, t, J=7.0 Hz), 3.73 (2H, t, J=7.0 Hz), 4.52 (2H, s), 5.13 (2H, s), 6.92 (1H, d, J=8.5 Hz), 7.20–7.40 (10H, m), 7.83 (1H, dd, J=8.5, 2.3 Hz), 7.86 (1H, d, J=2.3 Hz)

4'-Benzyloxy-3'-(2-benzyloxyethyl)acetophenone (8.0 g) and 0.4 ml of 30% hydrogen bromide acetic acid solution were dissolved in 80 ml of chloroform, and a solution of 1.1 ml of bromine in 30 ml of chloroform was added to the solution dropwise during 2 hours with stirring at room temperature. The reaction solution was concentrated under reduced pressure and the resulting residue was purified by silica gel medium pressure liquid column chromatography (eluent: hexane/diethyl ether=2/1) to give 3.9 g of 4'-benzyloxy-3'-(2-benzyloxyethyl)-2-bromoacetophenone having a melting point of 53 to 56° C.

IR (KBr): 1684 cm$^{-1}$; $^1$H-NMR (CDCl$_3$); δ ppm: 3.04 (2H, t, J=6.9 Hz), 3.73 (2H, t, J=6.9 Hz), 4.38 (2H, s), 4.51 (2H, s), 5.14 (2H, s), 6.95 (1H, d, J=8.4 Hz), 7.20–7.45 (10H, m), 7.85–7.90 (2H, m)

Water (20 ml) and methylene chloride (20 ml) were added to 600 mg of ethyl (S)-2-(2-amino-1,2,3,4-tetrahydronaphthalen-7-yloxy)acetate hydrochloride, 300 mg of sodium bicarbonate was added to the mixture with stirring under ice-cooling, and the mixture was stirred for 30 minutes. The organic layer was separated and dried over anhydrous magnesium sulfate, and the solvent was evaporated under reduced pressure. The resulting residue was dissolved in 0.5 ml of N,N-dimethylformamide, a solution of 440 mg of 4'-benzyloxy-3'-(2-benzyloxyethyl)-2-bromoacetophenone in 1 ml of N,N-dimethylformamide was added to the solution with stirring at −10° C., and the mixture was subjected to 20 minutes of reaction at 0° C. The reaction solution was again cooled to −10° C., 190 mg of sodium borohydride and 4 ml of ethanol were added to the solution with stirring in that order, and the mixture was subjected to 10 minutes of reaction at 0° C. The reaction mixture was poured into ice water and the mixture was extracted with ethyl acetate. The extract was washed with water and dried over anhydrous magnesium sulfate, and then the solvent was evaporated under reduced pressure. The resulting residue was dissolved in 10 ml of tetrahydrofuran, 0.7 ml of triethanolamine was added to the solution, and the mixture was heated under reflux for 16 hours. After cooling, water was added and the mixture was extracted with ethyl acetate. The extract was washed with water and then dried over anhydrous magnesium sulfate. The solvent was evaporated under reduced pressure and the resulting residue was purified by silica gel medium pressure liquid column chromatography (eluent: methylene chloride/ethanol=30/1) to give 540 mg of ethyl 2-[(2S)-2-[[(2RS)-2-[4-benzyloxy-3-(2-benzyloxyethyl)phenyl]-2-hydroxyethyl]amino]-1,2,3,4-tetrahydronaphthalen-7-yloxy]acetate in an oily form.

IR (neat): 3297, 1759, 1736 cm$^{-1}$; $^1$H-NMR (CDCl$_3$); δ ppm: 1.30 (3H, t, J=7.1 Hz), 1.50–1.65 (1H, m), 2.00–2.10 (1H, m), 2.50–2.85 (4H, m), 2.90–3.10 (5H, m), 3.72 (2H, t, J=7.3 Hz), 4.27 (2H, q, J=7.1 Hz), 4.51 (2H, s), 4.57 (2H, s), 4.62 (1H, dd, J=9.0, 3.4 Hz), 5.06 (2H, s), 6.60 (1H, s), 6.69 (1H, dd, J=8.4, 2.7 Hz), 6.88 (1H, d, J=8.4 Hz), 6.99 (1H, d, J=8.4 Hz), 7.15–7.45 (12H, m)

Ethyl 2-[(2S)-2-[[(2RS)-2-[4-benzyloxy-3-(2-benzyloxyethyl)phenyl]-2-hydroxyethyl]amino]-1,2,3,4-tetrahydronaphthalen-7-yloxy]acetate (256 mg) and 2.2 ml of dimethylamine were dissolved in 2.2 ml of tetrahydrofuran, and the solution was sealed in a tube and subjected to 39 hours of reaction at 60° C. The reaction solution was concentrated under reduced pressure and the resulting residue was purified by silica gel medium pressure liquid column chromatography (eluent: ethyl acetate/ethanol=1/1) to give 230 mg of amorphous 2-[(2S)-2-[[(2RS)-2-[4-benzyloxy-3-(2-benzyloxyethyl)phenyl]-2-hydroxyethyl]amino]-1,2,3,4-tetrahydronaphthalen-7-yloxy]-N,N-dimethylacetamide.

IR (neat): 3381, 1655, 1649 cm$^{-1}$; $^1$H-NMR (CDCl$_3$); δ ppm: 1.60–1.75 (1H, m), 2.05–3.15 (18H, m), 3.71 (2H, t, J=7.2 Hz), 4.50 (2H, s), 4.63 (2H, s), 4.75 (1H, d, J=7.4 Hz), 5.05 (2H, s), 6.63 (1H, s), 6.74 (1H, dd, J=8.4, 2.7 Hz), 6.87 (1H, d, J=8.4 Hz), 6.99 (1H, d, J=8.4 Hz), 7.15–7.45 (12H, m)

Reference Example 8
(−)-2-[(2S)-2-[[(2R)-2-[4-Benzyloxy-3-(2-benzyloxyethyl)-phenyl]-2-hydroxyethyl]amino]-1,2,3,4-tetrahydronaphthalen-7-yloxy]-N,N-dimethylacetamide Benzyl 2-(2-benzyloxyethyl)phenyl ether (159 mg) and 123 mg of sodium acetate was suspended in 2 ml of acetic acid, 29 μl of bromine was added to the suspension with stirring at room temperature, and the mixture was subjected to 1 hour of reaction. Then, a solution of 100 mg of sodium sulfite heptahydrate in 20 ml of water was added, and the mixture was extracted with ethyl acetate. The extract was washed with water, an aqueous saturated sodium bicarbonate solution and water in that order and then dried over anhydrous magnesium sulfate. The solvent was evaporated under reduced pressure and the resulting residue was purified by silica gel medium pressure liquid column chromatography (eluent: hexane/methylene chloride=2/1) to give 173 mg of benzyl 2-(2-benzyloxyethyl)-4-bromophenyl ether in an oily form.

$^1$H-NMR (CDCl$_3$); δ ppm: 2.97 (2H, t, J=7.0 Hz), 3.68 (2H, t, J=7.0 Hz), 4.50 (2H, s), 5.02 (2H, s), 6.75 (1H, d, J=8.7 Hz), 7.20–7.40 (12H, m)

Benzyl 2-(2-benzyloxyethyl)-4-bromophenyl ether (24.0 g) was dissolved in 200 ml of tetrahydrofuran, 47.0 ml of 1.57 M n-butyl lithium in hexane was added to the solution with stirring at −95° C., and the mixture was subjected to 15 minutes of reaction. The reaction solution was added to a solution of 10.8 g of diethyl oxalate in 300 ml of tetrahydrofuran with stirring at −95° C., and the resulting solution was subjected to 1 hour of reaction. Then, 200 ml of ethanol and 755 mg of sodium borohydride were added in that order. The reaction solution was stirred at −35° C. for 45 minutes, 4.70 ml of acetic acid was added, and the mixture was stirred for 15 minutes. Then, a solution of 6.9 g of sodium bicarbonate in 300 ml of water was added and then the mixture was concentrated under reduced pressure. The resulting concentrate was extracted with ethyl acetate, and the extract was washed with water and then dried over anhydrous magnesium sulfate. Thereafter, the solvent was evaporated under reduced pressure and the resulting residue was purified by silica gel medium pressure liquid column chromatography (eluent: hexane/ethyl acetate=3/1) to give 19.9 g of ethyl 2-[4-benzyloxy-3-(2benzyloxyethyl)phenyl]-2-hydroxyacetate in an oily form.

IR (neat): 3456, 1735 cm$^{-1}$; $^1$H-NMR (CDCl$_3$); δ ppm: 1.21 (3H, t, J=7.1 Hz), 3.02 (2H, t, J=7.3 Hz), 3.34 (1H, d, J=5.9 Hz), 3.70 (2H, t, J=7.3 Hz), 4.10–4.30 (2H, m), 4.51 (2H, s), 5.05 (2H, s), 5.08 (1H, d, J=5.9 Hz), 6.87 (1H, d, J=8.4 Hz), 7.20–7.40 (12H, m)

Ethyl 2-[4-benzyloxy-3-(2-benzyloxyethyl)phenyl]-2-hydroxyacetate (39.7 g) was suspended in 40 ml of ethanol, 57 ml of 2 N aqueous sodium hydroxide solution was added to the suspension with stirring under ice-cooling, and the mixture was subjected to 1 hour of reaction at room temperature. Then, 57 ml of 2 N aqueous sulfuric acid solution was added to the reaction solution with stirring under ice-cooling, and the mixture was extracted with ethyl acetate. The extract was washed with water and then dried over anhydrous magnesium sulfate. Thereafter, the solvent was evaporated under reduced pressure to give 35.1 g of 2-[4-benzyloxy-3-(2-benzyloxyethyl)phenyl]-2-hydroxyacetic acid in an oily form.

IR (neat): 3399, 1734, 1719 cm$^{-1}$; $^1$H-NMR (CDCl$_3$); δ ppm: 3.01 (2H, t, J=7.1 Hz), 3.71 (2H, t, J=7.1 Hz), 4.50 (2H, s), 5.06 (2H, s), 5.16 (1H, s), 6.89 (1H, d, J=8.4 Hz), 7.20–7.40 (12H, m)

2-[4-Benzyloxy-3-(2-benzyloxyethyl)phenyl]-2-hydroxyacetic acid (1.73 g), 1.18 g of (S)-2-amino-7-hydroxytetralin hydrobromide and 1.95 g of benzotriazol-1-yloxytris(dimethylamino)phosphonium hexafluorophosphate were dissolved in 11 ml of N,N-dimethylformamide, 1.23 ml of triethylamine was added to the solution with stirring at room temperature and the mixture was subjected to 3 hours of reaction. Water was added to the reaction solution and the mixture was extracted with ethyl acetate. The extract was washed with water and then dried over anhydrous magnesium sulfate. The solvent was evaporated under reduced pressure and the resulting residue was partially purified by silica gel medium pressure liquid column chromatography (eluent: hexane/ethyl acetate=1/1) to give 2-[4-benzyloxy-3-(2-benzyloxyethyl)phenyl]-2-hydroxy-N-((2S)-7-hydroxy-1,2,3,4-tetrahydronaphthalen-2yl)acetamide (diastereomer mixture). The mixture was separated by silica gel medium pressure liquid column chromatography (eluent: diethyl ether) to give 1.08 g of amorphous (−)-(2R)-2-[4-benzyloxy-3-(2-benzyloxyethyl)phenyl]-2-hydroxy-N-((2S)-7-hydroxy-1,2,3,4-tetrahydronaphthalen-2-yl)acetamide (low polarity isomer) and 0.94 g of amorphous (−)-(2S)-2-[4benzyloxy-3-(2-benzyloxyethyl)phenyl]-2-hydroxy-N-((2S)-7-hydroxy-1,2,3,4-tetrahydronaphthalen-2-yl)acetamide (high polarity isomer).

Low polarity isomer

IR (film): 3382, 1650 cm$^{-1}$; $^1$H-NMR (CDCl$_3$); δ ppm: 1.60–1.75 (1H, m), 1.85–2.00 (1H, m), 2.51 (1H, dd, J=16.3, 7.7 Hz), 2.55–2.80 (2H, m), 2.85–3.05 (3H, m), 3.49 (1H, d, J=3.3 Hz), 3.66 (2H, t, J=7.4 Hz), 4.15–4.25 (1H, m), 4.47 (2H, s), 4.89 (1H, d, J=3.3 Hz), 5.00 (2H, s), 6.32 (1H, br s), 6.37 (1H, d, J=2.5 Hz), 6.49 (1H, d, J=8.0 Hz), 6.56 (1H, dd, J=8.3, 2.5 Hz), 6.81 (1H, d, J=8.4 Hz), 6.85 (1H, d, J=8.3 Hz), 7.10 (1H, d, J=2.2 Hz), 7.14 (1H, dd, J=8.4, 2.2 Hz), 7.20–7.40 (10H, m); Specific rotation: $[α]_D^{31}$=−59.5° (c=1.08, MeOH)

High polarity isomer

IR (film): 3387, 1655 cm$^{-1}$; $^1$H-NMR (CDCl$_3$); δ ppm: 1.60–1.75 (1H, m), 1.90–2.00 (1H, m), 2.49 (1H, dd, J=16.3, 8.3 Hz), 2.65–2.80 (2H, m), 2.90–3.05 (3H, m), 3.57 (1H, br s), 3.69 (2H, t, J=7.1 Hz), 4.15–4.25 (1H, m), 4.49 (2H, s), 4.91 (1H, d, J=3.4 Hz), 5.02 (2H, s), 6.02 (1H, br s), 6.35–6.45 (2H, m), 6.59 (1H, dd, J=8.3, 2.6 Hz), 6.84 (1H, d, J=8.4 Hz), 6.88 (1H, d, J=8.3 Hz), 7.10–7.40 (12H, m) Specific rotation: $[α]_D^{31}$=−4.8° (c=1.05, MeOH)

(−)-(2R)-2-[4-Benzyloxy-3-(2-benzyloxyethyl)phenyl]-2-hydroxy-N-((2S)-7-hydroxy-1,2,3,4-tetrahydronaphthalen-2-yl)acetamide (low polarity isomer) (1.08 g) was dissolved in 20 ml of tetrahydrofuran, 438 μl of borane-dimethylsulfide complex was added to the solution, and the mixture was heated under reflux for 3 hours. Then, a solution of 1.14 g of triethanolamine in 1 ml of tetrahydrofuran was added and the mixture was again heated under reflux for 6 hours. After cooling, water was added to the reaction solution, and the mixture was extracted with ethyl acetate. The extract was washed with water and then dried over anhydrous magnesium sulfate. Thereafter, the solvent was evaporated under reduced pressure and the resulting residue was recrystallized from ethyl acetate to give 687 mg of (−)-(1R)-1-[4-benzyloxy-3-(2-benzyloxyethyl)phenyl]-2-((2S)-7-hydroxy-1,2,3,4-tetrahydronaphthalen-2-ylamino) ethanol having a melting point of 147 to 150° C.

IR (KBr): 3430, 3290, 3190 cm$^{-1}$; $^1$H-NMR (CDCl$_3$); δ ppm: 1.50–1.65 (1H, m), 2.00–2.10 (1H, m), 2.54 (1H, dd, J=17.7, 10.6 Hz), 2.65–2.85 (3H, m), 2.90–3.10 (5H, m), 3.72 (2H, t, J=7.2 Hz), 4.51 (2H, s), 4.62 (1H, dd, J=9.0, 3.4 Hz), 5.05 (2H, s), 6.52 (1H, d, J=2.6 Hz), 6.60 (1H, dd, J=8.2, 2.6 Hz), 6.87 (1H, d, J=8.3 Hz), 6.94 (1H, d, J=8.2

Hz), 7.15–7.40 (12H, m); Specific rotation: $[\alpha]_D^{31}$=−47.9° (c=1.10, tetrahydrofuran)

(−)-(1R)-1-[4-Benzyloxy-3-(2-benzyloxyethyl)phenyl]-2-((2S)-7-hydroxy-1,2,3,4-tetrahydronaphthalen-2-ylamino)ethanol (450 mg) was dissolved in 4 ml of methylene chloride, 860 μl of 5 N aqueous sodium hydroxide solution and 143 mg of 2-bromo-N,N-dimethylacetamide were added to the solution with stirring at room temperature in that order, and the mixture was subjected to 3 hours of reaction at room temperature. Then, 143 mg of 2-bromo-N,N-dimethylacetamide was additionally added to the reaction solution, and the mixture was subjected to 1 hour of reaction at room temperature. Then, 267 μl of diethylamine was added and the mixture was stirred for 30 minutes. Brine was added to the reaction solution, and the mixture was extracted with ethyl acetate. The extract was washed with brine and then dried over anhydrous magnesium sulfate. The solvent was evaporated under reduced pressure and the resulting residue was purified by aminopropylated silica gel medium pressure liquid column chromatography (eluent: ethyl acetate) to give 410 mg of (−)-2-[(2S)-2-[[(2R)-2-[4-benzyloxy-3-(2-benzyloxyethyl)phenyl]-2-hydroxyethyl]amino]-1,2,3,4-tetrahydronaphthalen-7-yloxy)-N,N-dimethylacetamide in an oily form.

IR (neat): 3410, 1656 cm$^{-1}$; $^1$H-NMR (CDCl$_3$); δ ppm: 1.50–1.65 (1H, m), 2.00–2.10 (1H, m), 2.56 (1H, dd, J=15.7, 8.4 Hz), 2.65–3.10 (14H, m), 3.72 (2H, t, J=7.5 Hz), 4.51 (2H, s), 4.60–4.70 (3H, m), 5.06 (2H, s), 6.58 (1H, d, J=2.7 Hz), 6.74 (1H, dd, J=8.4, 2.7 Hz), 6.88 (1H, d, J=8.4 Hz), 6.99 (1H, d, J=8.4 Hz), 7.15–7.45 (12H, m) Specific rotation: $[\alpha]_D^{25}$=−41.1° (c=1.00, MeOH)

Reference Example 9

(−)-2-[(2S)-2-[[(2S)-2-[4-Benzyloxy-3-(2-benzyloxyethyl)-phenyl]-2-hydroxyethyl]amino]-1,2,3,4-tetrahydronaphthalen-7-yloxy)-N,N-dimethylacetamide Using (−)-(2S)-2-[4-benzyloxy-3-(2-benzyloxyethyl)-phenyl]-2-hydroxy-N-((2S)-7-hydroxy-1,2,3,4-tetrahydronaphthalen-2-yl)acetamide (high polarity isomer) obtained in Reference Example 8, the reactions and treatments of Reference Example 8 were repeated to give (−)-2-[(2S)-2-[[(2S)-2-[4-benzyloxy-3-(2-benzyloxyethyl)phenyl]-2-hydroxyethyl]amino]-1,2,3,4-tetrahydronaphthalen-7-yloxy)-N,N-dimethylacetamide in an oily form.

IR (neat): 3409, 1655 cm$^{-1}$; $^1$H-NMR (CDCl$_3$); δ ppm: 1.50–1.65 (1H, m), 2.00–2.10 (1H, m), 2.57 (1H, dd, J=16.0, 8.8 Hz), 2.65–3.10 (14H, m), 3.71 (2H, t, J=7.2 Hz), 4.50 (2H, s), 4.55–4.65 (3H, m), 5.05 (2H, s), 6.64 (1H, d, J=2.7 Hz), 6.73 (1H, dd, J=8.4, 2.7 Hz), 6.87 (1H, d, J=8.4 Hz), 6.98 (1H, d, J=8.4 Hz), 7.15–7.45 (12H, m); Specific rotation: $[\alpha]_D^{31}$=−24.2° (c=1.08, MeOH)

(−)-1-[2-[(2S)-2-[[(2R)-2-[4-Benzyloxy-3-(2-benzyloxyethyl)-phenyl]-2-hydroxyethyl]amino]-1,2,3,4-tetrahydronaphthalen-7-yloxy]acetyl]pyrrolidine Using (−)-(2R)-2-[4-benzyloxy-3-(2-benzyloxyethyl)-phenyl]-2-hydroxy-N-((2S)-7-hydroxy-1,2,3,4-tetrahydronaphthalen-2-yl)acetamide (low polarity isomer) obtained in Reference Example 8 and 1-bromoacetylpyrrolidine, the reactions and treatments of Reference Example 8 were repeated to give (−)-1-[2-[(2S)-2-[[(2R)-2-[4-benzyloxy-3-(2-benzyloxyethyl)-phenyl]-2-hydroxyethyl]amino]-1,2,3,4-tetrahydronaphthalen-7-yloxy]acetyl]pyrrolidine in an oily form.

IR (neat): 3401, 1652 cm$^{-1}$; $^1$H-NMR (CDCl$_3$); δ ppm: 1.40–1.75 (1H, m), 1.80–2.10 (5H, m), 2.50–2.60 (1H, m), 2.65–3.10 (8H, m), 3.45–3.55 (4H, m), 3.72 (2H, t, J=7.3 Hz), 4.51 (2H, s), 4.55–4.65 (3H, m), 5.06 (2H, s), 6.65 (1H, d, J=2.7 Hz), 6.74 (1H, dd, J=8.4, 2.7 Hz), 6.88 (1H, d, J=8.4 Hz), 6.99 (1H, d, J=8.4 Hz), 7.15–7.45 (12H, m); Specific rotation: $[\alpha]_D^{25}$=−41.4° (c=0.59, MeOH)

(−)-1-[2-[(2S)-2-[[(2R)-2-[4-Benzyloxy-3-(2-benzyloxyethyl)phenyl]-2-hydroxyethyl]amino]-1,2,3,4-tetrahydronaphthalen-7-yloxy]acetyl]piperidine Using (−)-(2R)-2-[4-benzyloxy-3-(2-benzyloxyethyl)phenyl]-2-hydroxy-N-((2S)-7-hydroxy-1,2,3,4-tetrahydronaphthalen-2-yl)acetamide (low polarity isomer) obtained in Reference Example 8 and 1-bromoacetylpiperidine, the reactions and treatments of Reference Example 8 were repeated to give (−)-1-[2-[(2S)-2-[[(2R)-2-[4-benzyloxy-3-(2-benzyloxyethyl)-phenyl]-2-hydroxyethyl]amino]-1,2,3,4-tetrahydronaphthalen-7-yloxy]acetyl]piperidine in an oily form.

IR (neat): 3395, 1649 cm$^{-1}$; $^1$H-NMR (CDCl$_3$); δ ppm: 1.30–1.70 (9H, m), 1.95–2.05 (1H, m), 2.50–3.10 (9H, m), 3.45–3.60 (4H, m), 3.72 (2H, t, J=7.2 Hz), 4.51 (2H, s), 4.55–4.65 (3H, m), 5.06 (2H, s), 6.65 (1H, d, J=2.7 Hz), 6.73 (1H, dd, J=8.4, 2.7 Hz), 6.88 (1H, d, J=8.4 Hz), 6.95–7.05 (1H, m), 7.15–7.45 (12H, m); Specific rotation: $[\alpha]_D^{30}$=−78.1° (c=0.52, CHCl$_3$)

(−)-4-[2-[(2S)-2-[[(2R)-2-[4-Benzyloxy-3-(2-benzyloxyethyl)phenyl]-2-hydroxyethyl]amino]-1,2,3,4-tetrahydronaphthalen-7-yloxy]acetyl]morpholine Using (−)-(2R)-2-[4-benzyloxy-3-(2-benzyloxyethyl)-phenyl]-2-hydroxy-N-((2S)-7-hydroxy-1,2,3,4-tetrahydronaphalen-2-yl)acetamide (low polarity isomer) obtained in Reference Example 8 and 4-bromoacetylmorpholine, the reactions and treatments of Reference Example 8 were repeated to give (−)-4-[2-[(2S)-2-[[(2R)-2-[4-benzyloxy-3-(2-benzyloxyethyl)-phenyl]-2-hydroxyethyl]amino]-1,2,3,4-tetrahydronaphthalen-7yloxy]acetyl]morpholine in an oily form.

IR (neat): 3403, 1655, 1649 cm$^{-1}$; $^1$H-NMR (CDCl$_3$); δ ppm: 1.40–1.80 (4H, m), 2.00–2.10 (1H, m), 2.50–3.10 (9H, m), 3.40–3.75 (9H, m), 4.51 (2H, s), 4.55–4.65 (3H, m), 5.06 (2H, s), 6.64 (1H, d, J=2.7 Hz), 6.72 (1H, dd, J=8.4, 2.7 Hz), 6.88 (1H, d, J=8.4 Hz), 6.95–7.05 (1H, m), 7.15–7.45 (12H, m) Specific rotation: $[\alpha]_D^{30}$=−46.9° (c=0.52, CHCl$_3$)

Reference Example 10

Ethyl 2-[(2S)-2-[[(2RS)-2-hydroxy-2-(4-hydroxy-3-hydroxymethylphenyl)ethyl]amino]-1,2,3,4-tetrahydronaphthalen-7-yloxy]acetate Water (500 ml) and methylene chloride (1,000 ml) were added to 42.5 g of ethyl (S)-2-(2-amino-1,2,3,4-tetrahydronaphthalen-7-yloxy)acetate hydrochloride, 19.0 g of sodium bicarbonate was added to the mixture with stirring under ice-cooling, and the mixture was stirred for 1 hour. The organic layer was separated and dried over anhydrous magnesium sulfate and then the solvent was evaporated under reduced pressure. The resulting residue was dissolved in 370 ml of N,N-dimethylformamide, a solution of 21.0 g of 2-bromo-1-(2,2-dimethylbenzo[1,2-d]-1,3-dioxan-6-yl)-1-ethanone in 220 ml of N,N-dimethylformamide was added to the solution with stirring at −10° C., and the mixture was subjected to 1 hour of reaction at 0° C. The reaction solution was cooled to −10° C., 14.0 g of sodium borohydride and 180 ml of ethanol were added to the solution with stirring in that order, and the mixture was subjected to 1 hour of reaction at 0° C. The reaction mixture was poured into ice-water, and the mixture was extracted with ethyl acetate. The extract was washed with water and then dried over anhydrous magnesium sulfate, and the solvent was evaporated under reduced pressure. The resulting residue was dissolved in 350 ml of tetrahydrofuran, 22 g of triethanolamine was added to the solution, and the mixture was heated under reflux for 12 hours. After cooling, water was added to the reaction solution, and the mixture was extracted with ethyl acetate. The extract was washed with water and then dried over anhydrous magnesium sulfate. Thereafter, the solvent was evaporated under reduced pressure and the resulting residue was purified by silica gel medium pressure liquid column chromatography (eluent: ethyl acetate/ethanol=7/1) to give 12.7 g of amorphous ethyl 2-[(2S)-2-[[(2RS)-2-(2,2-dimethylbenzo[1,2-d]-1,3-dioxan-6-yl)-2-hydroxyethyl]-amino]-1,2,3,4-tetrahydronaphthalen-7-yloxy]acetate.

IR (KBr): 3304, 1758, 1737 cm$^{-1}$; $^1$H-NMR (CDCl$_3$); δ ppm: 1.30 (3H, t, J=7.1 Hz), 1.45–1.70 (7H, m), 2.00–2.10 (1H, m), 2.50–3.10 (7H, m), 4.27 (2H, q, J=7.1 Hz), 4.55–4.65 (3H, m), 4.84 (2H, s), 6.61 (1H, s), 6.69 (1H, dd, J=8.4, 2.6 Hz), 6.79 (1H, d, J=8.4 Hz), 6.99 (1H, d, J=8.4 Hz), 7.02 (1H, s), 7.13 (1H, d, J=8.4 Hz)

Ethyl 2-[(2S)-2-[[(2RS)-2-(2,2-dimethylbenzo[1,2-d]-1,3-dioxan-6-yl)-2-hydroxyethyl]amino]-1,2,3,4-tetrahydronaphthalen-7-yloxy]acetate (11.5 g) was suspended in 75 ml of 1,2-dimethoxyethane, 252 ml of 1 N hydrochloric acid was added dropwise to the suspension while keeping the temperature at 20° C. or lower, and the resulting mixture was subjected to 30 minutes of reaction at room temperature. Then, 23.3 g of sodium bicarbonate was added with stirring at 0° C., and the mixture was extracted with ethyl acetate. The extract was washed with an aqueous saturated sodium bicarbonate solution and brine and then dried over anhydrous magnesium sulfate. Thereafter, the solvent was evaporated under reduced pressure and the resulting residue was purified by silica gel medium pressure liquid column chromatography (eluent: ethyl acetate/ethanol=5/1) to give 7.2 g of amorphous ethyl 2-[(2S)-2-[[(2RS)-2-hydroxy-2-(4-hydroxy-3-hydroxymethylphenyl)ethyl]-amino]-1,2,3,4-tetrahydronaphthalen-7-yloxy]acetate.

IR (KBr): 3191, 1763, 1752, 1738 cm$^{-1}$; $^1$H-NMR (DMSO-d$_6$); δ ppm: 1.15–1.25 (3H, m), 1.35–1.55 (1H, m), 1.70 (1H, br s), 1.85–2.00 (1H, m), 2.35–2.50 (1H, m), 2.55–3.00 (6H, m), 4.10–4.20 (2H, m), 4.40–4.55 (3H, m), 4.65–4.70 (2H, m), 4.94 (1H, br s), 5.08 (1H, br s), 6.55–6.70 (2H, m), 6.69 (1H, d, J=8.2 Hz), 6.95 (1H, d, J=8.2 Hz), 7.01 (1H, d, J=8.2 Hz), 7.25–7.30 (1H, m), 9.17 (1H, br s)

Reference Example 11

4-[(2S)-2-[[(2RS)-2-(2,2-Dimethylbenzo[1,2-d]-1,3-dioxan-6yl)-2-hydroxyethyl]amino]-1,2,3,4-tetrahydronapthalen-7-yloxy]-N,N-dimethylbutyramide (S)-4-(2-Amino-1,2,3,4-tetrahydronaphthalen-7-yloxy)-N,N-dimethylbutyramide (263 mg) and 360 μl of triethylamine were dissolved in 5 ml of N,N-dimethylformamide, a solution of 245 mg of 2-bromo-1-(2,2-dimethylbenzo[1,2-d]-1,3-dioxan-6-yl)-1-ethanone in 2 ml of N,N-dimethylformamide was added to the solution with stirring under ice-cooling, and the mixture was subjected to 25 minutes of reaction. With stirring under ice-cooling, 220 mg of sodium borohydride and 5 ml of ethanol were added to the reaction solution, and the mixture was stirred for 1.5 hours. The reaction solution was poured into ice-water, and the mixture was extracted with ethyl acetate. The extract was washed with water and then dried over anhydrous magnesium sulfate. The solvent was evaporated under reduced pressure, a solution of 260 mg of triethanolamine in 7 ml of tetrahydrofuran was added to the resulting residue, and the mixture was heated under reflux for 12 hours. Water was added to the reaction solution, and the mixture was extracted with ethyl acetate. The extract was washed with water and then dried over anhydrous magnesium sulfate. The solvent was evaporated under reduced pressure and the resulting residue was purified by silica gel medium pressure liquid column chromatography (eluent: ethyl acetate/ethanol=6/1) to give 165 mg of amorphous 4-[(2S)-2-[[(2RS)-2-(2,2-dimethylbenzo-[1,2-d]-1,3-dioxan-6-yl)-2-hydroxyethyl]amino]-1,2,3,4-tetrahydronaphthalen-7-yloxy]-N,N-dimethylbutyramide.

IR (KBr): 3445, 1631 cm$^{-1}$; $^1$H-NMR (CDCl$_3$); δ ppm: 1.53–1.70 (7H, m), 2.00–2.20 (3H, m), 2.45–3.10 (15H, m), 3.95–4.05 (2H, m), 4.60–4.65 (1H, m), 4.85 (2H, s), 6.60 (1H, s), 6.65–6.75 (1H, m), 6.80 (1H, d, J=8.4 Hz), 6.98 (1H, d, J=8.4 Hz), 7.03 (1H, s), 7.10–7.20 (1H, m)

Example 1

2-[(2S)-2-[[(2RS)-2-Hydroxy-2-(4-hydroxy-3-hydroxymethylphenyl)ethyl]amino]-1,2,3,4-tetrahydronaphthalen-7yloxy]-N,N-dimethylacetamide (Compound 1)

Ethyl 2-[(2S)-2-[[(2RS)-2-hydroxy-2-(4-hydroxy-3-hydroxymethylphenyl)ethyl]amino]-1,2,3,4-tetrahydronaphthalen-7-yloxy]acetate (2.00 g) was dissolved in a solution of 17.9 g of dimethylamine in 10 ml of tetrahydrofuran, and the solution was sealed in a tube and subjected to 36 hours of reaction at 65° C. The reaction solution was concentrated under reduced pressure and the resulting residue was purified by aminopropylated silica gel medium pressure liquid column chromatography (eluent: chloroform/methanol=10/1) to give 1.58 g of amorphous 2-[(2S)-2-[[(2RS)-2-hydroxy-2-(4-hydroxy-3-hydroxymethylphenyl)ethyl]amino]-1,2,3,4-tetrahydronaphthalen-7-yloxy]acetate-N,N-dimethylacetamide (Compound 1).

IR (KBr): 3395, 1652 cm$^{-1}$; $^1$H-NMR (CDCl$_3$); δ ppm: 1.50–1.65 (1H, m), 1.95–2.10 (1H, m), 2.45–2.60 (1H, m), 2.65–2.85 (3H, m), 2.85–3.00 (6H, m), 3.05–3.10 (3H, m), 4.55–4.70 (3H, m), 4.75–4.85 (2H, m), 6.55–6.65 (1H, m), 6.65–6.75 (1H, m), 6.80–6.85 (1H, m), 6.90–7.05 (2H, m), 7.10–7.20 (1H, m)

Example 2

The following compounds were obtained in the same manner as that described in Example 1.

2-[(2S)-2-[[(2RS)-2-Hydroxy-2-(4-hydroxy-3-hydroxymethylphenyl)ethyl]amino]-1,2,3,4-tetrahydronaphthalen-7-yloxyl]-acetamide (Compound 2)
Amorphous IR (KBr): 3410, 1666 cm$^{-1}$; $^1$H-NMR (DMSO-d$_6$); δ ppm: 1.40–1.75 (2H, m), 1.85–2.00 (1H, m), 2.40–3.00 (7H, m), 4.30–4.35 (2H, m), 4.40–4.55 (3H, m), 4.93 (1H, br s), 5.08 (1H, br s), 6.60–6.75 (3H, m), 6.90–7.05 (2H, m), 7.25–7.30 (1H, m), 7.35 (1H, br s), 7.44 (1H, br s), 9.15 (1H, br s)

4-[2-[(2S)-2-[[(2RS) -2-Hydroxy-2-(4-hydroxy-3-hydroxymethylphenyl)ethyl]amino]-1,2,3,4-tetrahydronaphthalen-7-yloxyl]-acetyl]morpholine (Compound 3)
Amorphous IR (KBr): 3400, 1645 cm$^{-1}$; $^1$H-NMR (DMSO-d$_6$); δ ppm: 1.35–1.80 (2H, m), 1.85–2.00 (1H, m), 2.35–2.95 (7H, m), 3.35–3.65 (8H, m), 4.40–4.55 (3H, m), 4.70–4.75 (2H, m), 4.89 (1H, br s), 5.03 (1H, br), 6.55–6.75 (3H, m), 6.90–7.05 (2H, m), 7.25–7.30 (1H, m), 9.13 (1H, br s)

1-[2-[(2S)-2-[[(2RS)-2-Hydroxy-2-(4-hydroxy-3-hydroxymethylphenyl)ethyl]amino]-1,2,3,4-tetrahydronaphthalen-7-yloxyl]-acetyl]piperidine (Compound 4)

Amorphous

IR (KBr): 3381, 1635 cm$^{-1}$; $^1$H-NMR (CDCl$_3$); δ ppm: 1.35–1.80 (7H, m), 1.95–2.10 (1H, m), 2.40–3.10 (7H, m), 3.40–3.65 (4H, m), 4.55–4.65 (3H, m), 4.85 (2H, s), 6.60–6.75 (2H, m), 6.80–6.90 (1H, m), 6.97 (1H, d, J=8.3 Hz), 7.06 (1H, d, J=2.1 Hz), 7.17 (1H, d, J=8.1 Hz)

1-[2-[(2S)-2-[[(2RS)-2-Hydroxy-2-(4-hydroxy-3-hydroxymethylphenyl)ethyl]amino]-1,2,3,4-tetrahydronaphthalen-7-yloxy]-acetyl]pyrrolidine (Compound 5)

Amorphous

IR (KBr): 3374, 3304, 1645 cm$^{-1}$; $^1$H-NMR (CDCl$_3$); δ ppm: 1.50–1.65 (1H, m), 1.80–2.10 (5H, m), 2.40–2.55 (1H, m), 2.65–3.00 (6H, m), 3.52 (4H, t, J=6.9 Hz), 4.50–4.65 (3H, m), 4.75–4.85 (2H, m), 6.55–6.75 (2H, m), 6.80–6.85 (1H, m), 6.95–7.05 (2H, m), 7.10–7.15 (1H, m)

Example 3

(−)-2-[(2S)-2-[[(2R)-2-Hydroxy-2-(4-hydroxy-3-hydroxymethylphenyl)ethyl]amino]-1,2,3,4-tetrahydronaphthalen-7-yloxy]-N,N-dimethylacetamide (Compound 6)

(−)-2-[(2S)-2-[[(2R)-2-(2,2-Dimethylbenzo[1,2-d]-1,3dioxan-6-yl)-hydroxyethyl]amino]-1,2,3,4-tetrahydronaphthalen-7-yloxy]-N,N-dimethylacetamide (192 mg) was dissolved in 3.8 ml of 1,2-dimethoxyethane, 4.2 ml of 1 N hydrochloric acid was added to the solution with stirring under ice-cooling, and the mixture was subjected to 2 hours of reaction at room temperature. The reaction solution was neutralized by adding an aqueous saturated sodium bicarbonate solution and then concentrated to dryness under reduced pressure. Tetrahydrofuran and ethanol were added to the resulting residue and insoluble materials were removed by filtration. The resulting filtrate was concentrated under reduced pressure, and the resulting residue was purified by aminopropylated silica gel medium pressure liquid column chromatography (eluent: ethyl acetate/ethanol=5/1) and then recrystallized from methanol to give 142 mg of (−)-2-[(2S)-2-[[(2R)-2-hydroxy-2-(4-hydroxy-3-hydroxymethylphenyl)ethyl]amino]-1,2,3,4-tetrahydronaphthalen- 7-yloxy]-N,N-dimethylacetamide (Compound 6) having a melting point of 175 to 176° C.

IR (KBr): 3363, 1648 cm$^{-1}$; $^1$H-NMR (DMSO-d$_6$); δ ppm: 1.40–1.50 (1H, m), 1.65 (1H, br s), 1.85–1.95 (1H, m), 2.43 (1H, dd, J=15.8, 8.4 Hz), 2.55–3.00 (12H, m), 4.40–4.55 (3H, m), 4.70 (2H, s), 4.95 (1H, br), 5.05–5.15 (1H, m), 6.55–6.70 (3H, m), 6.93 (1H, d, J=8.3 Hz), 7.00 (1H, dd, J=8.2, 2.0 Hz), 7.27 (1H, d, J=2.0 Hz), 9.20 (1H, br) Specific rotation: [α]$_D^{25}$=−80.0° (c=1.03, AcOH)

Example 4

(−)-1-[2-[(2S)-2-[[(2R)-2-Hydroxy-2-(4-hydroxy-3-hydroxymethylphenyl)ethyl]amino]-1,2,3,4-tetrahydronaphthalen-7-yloxy]acetyl]pyrrolidine (Compound 7)

Using (−)-1-[2-[(2S)-2-[[(2R)-2-(2,2-dimethylbenzo-[1,2-d]-1,3-dioxan-6-yl)-2-hydroxyethyl]amino]-1,2,3,4-tetrahydronaphthalen-7-yloxy]acetyl]pyrrolidine obtained in Reference Example 5, the procedure of Example 3 was repeated to give (−)-1-[2-[(2S)-2-[[(2R)-2-hydroxy-2-(4-hydroxy-3hydroxymethylphenyl)ethyl]amino]-1,2,3,4-tetrahydronaphthalen-7-yloxy]acetyl]pyrrolidine (Compound 7) having a melting point of 192 to 195° C. (recrystallization solvent: methanol).

IR (KBr): 3327, 1646 cm$^{-1}$; $^1$H-NMR (DMSO-d$_6$); δ ppm: 1.40–2.00 (7H, m), 2.43 (1H, dd, J=16.1, 8.7 Hz), 2.55–3.00 (6H, m), 3.31 (2H, t, J=6.8 Hz), 3.45 (2H, t, J=6.8 Hz), 4.40–4.55 (3H, m), 4.62 (2H, s), 4.93 (1H, br s), 5.08 (1H, d, J=3.7 Hz), 6.55–6.75 (3H, m), 6.93 (1H, d, J=8.3 Hz), 7.00 (1H, dd, J=8.2, 2.0 Hz), 7.27 (1H, d, J=2.0 Hz), 9.17 (1H, br s) Specific rotation: [α]$_D^{25}$=−71.3° (c=1.12, ACOH)

(−)-1-[2-[(2S)-2-[[(2S)-2-Hydroxy-2-(4-hydroxy-3-hydroxymethylphenyl)ethyl]amino]-1,2,3,4-tetrahydronaphthalen-7-yloxy]acetyl]pyrrolidine (Compound 8)

Using (−)-1-[2-[(2S)-2-[[(2S)-2-(2,2-dimethylbenzo-[1,2-d]-1,3-dioxan-6-yl)-2-hydroxyethyl]amino]-1,2,3,4-tetrahydronaphthalen-7-yloxy]acetyl]pyrrolidine obtained in Reference Example 6, the procedure of Example 3 was repeated to give amorphous (−)-1-[2-[(2S)-2-[[(2S)-2-hydroxy-2-(4hydroxy-3-hydroxymethylphenyl)ethyl]amino]-1,2,3,4-tetrahydronaphthalen-7-yloxy]acetyl]pyrrolidine (Compound 8).

IR (KBr): 3297, 1645 cm$^{-1}$; $^1$H-NMR (DMSO-d$_6$+H$_2$O); δ ppm: 1.40–1.50 (1H, m), 1.70–2.00 (5H, m), 2.41 (1H, dd, J=15.6, 8.4 Hz), 2.55–2.95 (6H, m), 3.28 (2H, t, J=6.8 Hz), 3.41 (2H, t, J=6.8 Hz), 4.45 (2H, s), 4.51 (1H, dd, J=8.4, 4.1 Hz), 4.59 (2H, s), 6.58 (1H, d, J=2.6 Hz), 6.63 (1H, dd, J=8.4, 2.6 Hz), 6.69 (1H, d, J=8.2 Hz), 6.93 (1H, d, J=8.4 Hz), 7.01 (1H, dd, J=8.2, 2.0 Hz), 7.25 (1H, d, J=2.0 Hz); Specific rotation: [α]$_D^{25}$=−45.8° (c=1.00, AcOH)

(−)-2-[(2S)-2-[[(2S)-2-Hydroxy-2-(4-hydroxy-3-hydroxymethylphenyl)ethyl]amino]-1,2,3,4-tetrahydronaphthalen-7-yloxy]-N,N-dimethylacetamide (Compound 9)

Using (−)-2-[(2S)-2-[[(2S)-2-(2,2-dimethylbenzo[1,2d]-1,3-dioxan-6-yl)-2-hydroxyethyl]amino]-1,2,3,4-tetrahydronaphthalen-7-yloxy]-N,N-dimethylacetamide obtained in Reference Example 6, the procedure of Example 3 was repeated to give amorphous (−)-2-[(2S)-2-[[(2S)-2-hydroxy-2-(4-hydroxy-3-hydroxymethylphenyl)ethyl]amino]-1,2,3,4-tetrahydronaphthalen-7-yloxy]-N,N-dimethylacetamide (Compound 9).

IR (film): 3297, 1650 cm$^{-1}$; $^1$H-NMR (CDCl$_3$); δ ppm: 1.50–1.65 (1H, m), 1.95–2.05 (1H, m), 2.46 (1H, dd, J=15.6, 8.7 Hz), 2.65–3.00 (9H, m), 3.07 (3H, s), 4.52 (1H, dd, J=8.8, 3.6 Hz), 4.62 (2H, s), 4.71 (2H, s), 6.58 (1H, d, J=2.6 Hz), 6.69 (1H, dd, J=8.4, 2.6 Hz), 6.78 (1H, d, J=8.3 Hz), 6.90–7.00 (2H, m), 7.07 (1H, dd, J=8.3, 1.9 Hz); Specific rotation: [α]$_D^{25}$=−25.6° (c=1.06, MeOH)

4-[(2S)-2-[[(2RS)-2-Hydroxy-2-(4-hydroxy-3-hydroxymethylphenyl)ethyl]amino]-1,2,3,4-tetrahydronaphthalen-7-yloxy]-N,N-dimethylbutramide (Compound 10)

Using 4-[2-[(2S)-2-[[(2RS)-2-(2,2-dimethylbenzo[1,2-d]-1,3-dioxan-6-yl)-2-hydroxyethyl]amino]-1,2,3,4-tetrahydronaphthalen-7-yloxy]-N,N-dimethylbutramide obtained in Reference Example 11, the procedure of Example 3 was repeated to give amorphous 4-[(2S)-2-[[(2RS)-2-hydroxy-2-(4-hydroxy- 3-hydroxymethylphenyl)ethyl]amino]-1,2,3,4-tetrahydronaphthalen-7-yloxy]-N,N-dimethylbutyramide (Compound 10).

IR (KBr): 3438, 1623 cm$^{-1}$; $^1$H-NMR (DMSO-d$_6$); δ ppm: 1.40–1.55 (1H, m), 1.85–2.00 (3H, m), 2.40–3.00 (16H, m), 3.85–3.95 (2H, m), 4.45–4.55 (3H, m), 4.90–5.00 (1H, m), 5.05–5.20 (1H, m), 6.60–6.75 (3H, m), 6.93 (1H, d, J=8.5 Hz), 7.01 (1H, d, J=6.8 Hz), 7.25–7.30 (1H, m), 9.17 (1H, br s)

(−)-4-[2-[(2S)-2-[[(2R)-2-Hydroxy-2-(4-hydroxy-3-hydroxymethylphenyl)ethyl]amino]-1,2,3,4-tetrahydronaphthalen-7-yloxy]acetyl]morpholine (Compound 11)

Using (−)-4-[2-[(2S)-2-[[(2R)-2-(2,2-dimethylbenzo[1,2-d]-1,3-dioxan-6-yl)-2-hydroxyethyl]amino]-1,2,3,4-tetrahydronaphthalen-7-yloxy]acetyl]morpholine obtained in Reference Example 5, the procedure of Example 3 was repeated to give amorphous (−)-4-[2-[(2S)-2-[[(2R)-2-hydroxy-2-(4hydroxy-3-hydroxymethylphenyl)ethyl]amino]-1,2,3,4-tetrahydronaphthalen-7-yloxy]acetyl]morpholine (Compound 11).

IR (KBr): 3400, 1647 cm$^{-1}$; $^1$H-NMR (DMSO-d$_6$); δ ppm: 1.35–1.75 (2H, m), 1.85–1.95 (1H, m), 2.30–3.00 (7H, m), 3.40–3.65 (8H, m), 4.40–4.55 (3H, m), 4.73 (2H, s), 4.90–5.00 (1H, m), 5.08 (1H, d, J=3.9 Hz), 6.60–6.75 (3H, m), 6.94 (1H, d, J=8.2 Hz), 7.00 (1H, dd, J=8.2, 1.8 Hz), 7.27 (1H, d, J=1.8 Hz), 9.18 (1H, br s); Specific rotation: $[α]_D^{25}$=−53.2° (c=0.53, MeOH)

(−)-1-[2-[(2S)-2-[[(2R)-2-Hydroxy-2-(4-hydroxy-3-hydroxymethylphenyl)ethyl]amino]-1,2,3,4-tetrahydronaphthalen-7-yloxy]acetyl]piperidine (Compound 12)

Using (−)-1-[2-[(2S)-2-[[(2R)-2-(2,2-dimethylbenzo[1,2-d]-1,3-dioxan-6-yl)-2-hydroxyethyl]amino]-1,2,3,4-tetrahydronaphthalen-7-yloxy]acetyl]piperidine obtained in Reference Example 5, the procedure of Example 3 was repeated to give (−)-1-[2-[(2S)-2-[[(2R)-2-hydroxy-2-(4-hydroxy-3-hydroxymethylphenyl)ethyl]amino]-1,2,3,4-tetrahydronaphthalen-7-yloxy]acetyl]piperidine (Compound 12) having a melting point of 167 to 170° C. (not recrystallized).

IR (KBr): 3346, 1645 cm$^{-1}$; $^1$H-NMR (DMSO-d$_6$); δ ppm: 1.35–1.80 (8H, m), 1.85–1.95 (1H, m), 2.35–2.95 (7H, m), 3.30–3.45 (4H, m), 4.40–4.55 (3H, m), 4.68 (2H, s), 4.93 (1H, br), 5.07 (1H, br s), 6.62 (1H, d, J=2.4 Hz), 6.64 (1H, dd, J=8.2, 2.7 Hz), 6.69 (1H, d, J=8.2 Hz), 6.94 (1H, d, J=8.3 Hz), 7.00 (1H, dd, J=8.2, 2.2 Hz), 7.27 (1H, d, J=2.0 Hz), 9.17 (1H, br); Specific rotation: $[α]_D^{25}$=−60.3° (c=0.50, MeOH)

Example 5

(−)-2-[(2S)-2-[[(2R)-2-Hydroxy-2-[4-hydroxy-3-(2-hydroxyethyl)phenyl]ethyl]amino]-1,2,3,4-tetrahydronaphthalen-7-yloxy]-N,N-dimethylacetamide (Compound 13)

(−)-2-[(2S)-2-[[(2R)-2-[4-Benzyloxy-3-(2-benzyloxyethyl)phenyl]-2-hydroxyethyl]amino]-1,2,3,4-tetrahydronaphthalen-7-yloxy]-N,N-dimethylacetamide (390 mg) obtained in Reference Example 8 and 30 mg of 10% palladium-carbon were suspended in 3 ml of acetic acid and the mixture was stirred at room temperature for 16 hours in an atmosphere of hydrogen. The catalyst was removed by filtration, the filtrate was concentrated under reduced pressure, and the resulting residue was purified by aminopropylated silica gel medium pressure liquid column chromatography (eluent; ethyl acetate/ethanol=5/1) to give 235 mg of amorphous (−)-2-[(2S)-2-[[(2R)-2-hydroxy-2-[4-hydroxy-3-(hydroxyethyl)phenyl]ethyl]amino]-1,2,3,4-tetrahydronaphthalen-7-yloxy]-N,N-dimethylacetamide (Compound 13).

IR (KBr): 3310, 1654 cm$^{-1}$; $^1$H-NMR (CDCl$_3$); δ ppm: 1.50–1.65 (1H, m), 1.95–2.10 (1H, m), 2.52 (1H, dd, J=17.5, 9.8 Hz), 2.65–3.05 (11H, m), 3.09 (3H, s), 3.90–4.00 (2H, m), 4.61 (1H, dd, J=8.8, 3.8 Hz), 4.64 (2H, s), 6.62 (1H, d, J=2.7 Hz), 6.71 (1H, dd, J=8.4, 2.7 Hz), 6.87 (1H, d, J=8.2 Hz), 6.98 (1H, d, J=8.4 Hz), 7.05–7.15 (2H, m); Specific rotation: $[α]_D^{25}$=−59.6° (c=1.10, MeOH)

Example 6

(−)-2-[(2S)-2-[[(2S)-2-Hydroxy-2-[4-hydroxy-3-(2-hydroxyethyl)phenyl]ethyl]amino]-1,2,3,4-tetrahydronaphthalen-7-yloxy]-N,N-dimethylacetamide (Compound 14)

Using (−)-2-[(2S)-2-[[(2S)-2-[4-benzyloxy-3-(2-benzyloxyethyl)phenyl]-2-hydroxyethyl]amino]-1,2,3,4-tetrahydronaphthalen-7-yloxy]-N,N-dimethylacetamide obtained in Reference Example 9, the procedure of Example 5 was repeated to give amorphous (−)-2-[(2S)-2-[[(2S)-2-hydroxy-2-[4-hydroxy-3-(2-hydroxyethyl)phenyl]ethyl]amino]-1,2,3,4-tetrahydronaphthalen-7-yloxy]-N,N-dimethylacetamide (Compound 14).

IR (film): 3292, 1652 cm$^{-1}$; $^1$H-NMR (CDCl$_3$); δ ppm: 1.50–1.65 (1H, m), 1.95–2.05 (1H, m), 2.43 (1H, dd, J=15.7, 9.1 Hz), 2.65–2.95 (8H, m), 2.96 (3H, s), 3.06 (3H, s), 3.79 (2H, br s), 4.57 (1H, dd, J=8.8, 3.6 Hz), 4.61 (2H, s), 6.57 (1H, d, J=2.6 Hz), 6.68 (1H, dd, J=8.4, 2.6 Hz), 6.78 (1H, d, J=8.0 Hz), 6.95–7.05 (3H, m); Specific rotation: $[α]_D^{31}$=−28.7° (c=1.12, MeOH)

2-[(2S)-2-[[(2RS)-2-Hydroxy-2-[4-hydroxy-3-(2-hydroxyethyl)-phenyl]ethyl]amino]-1,2,3,4-tetrahydronaphthalen-7-yloxy]-N,N-dimethylacetamide (Compound 15)

Using 2-[(2S)-2-[[(2RS)-2-[4-benzyloxy-3-(2benzyloxyethyl)phenyl]-2-hydroxyethyl]amino]-1,2,3,4-tetrahydronaphthalen-7-yloxy]-N,N-dimethylacetamide obtained in Reference Example 7, the procedure of Example 5 was repeated to give amorphous 2-[(2S)-2-[[(2RS)-2-hydroxy-2-[4hydroxy-3-(2-hydroxyethyl)phenyl]ethyl]amino]-1,2,3,4-tetrahydronaphthalen-7-yloxy]-N,N-dimethylacetamide (Compound 15).

IR (KBr): 3416, 1649 cm$^{-1}$; $^1$H-NMR (CDCl$_3$); δ ppm: 1.55–1.70 (1H, m), 2.00–2.10 (1H, m), 2.50–3.15 (18H, m), 3.50 (1H, br s), 3.96 (2H, t, J=5.3 Hz), 4.55–4.70 (3H, m), 6.61 (1H, s), 6.71 (1H, dd, J=8.4, 2.5 Hz), 6.87 (1H, d, J=8.1 Hz), 6.98 (1H, d, J=8.4 Hz), 7.05–7.15 (2H, m)

(−)-1-[2-[(2S)-2-[[(2R)-2-Hydroxy-2-[4-hydroxy-3-(2-hydroxyethyl)phenyl]ethyl]amino]-1,2,3,4-tetrahydronaphthalen-7-yloxy]acetyl]pyrrolidine (Compound 16)

Using (−)-1-[2-[(2S)-2-[[(2R)-2-[4-benzyloxy-3-(2benzyloxyethyl)phenyl]-2-hydroxyethyl]amino]-1,2,3,4-tetrahydronaphthalen-7-yloxy]acetyl]pyrrolidine obtained in Reference Example 9, the procedure of Example 5 was repeated to give amorphous (−)-1-[2-[(2S)-2-[[(2R)-2-[4-hydroxy-3-(2-hydroxyethyl)phenyl]-2-2-hydroxyethyl]amino]-1,2,3,4-tetrahydronaphthalen-7-yloxy]acetyl]pyrrolidine (Compound 16).

IR (KBr): 3409, 1643 cm$^{-1}$; $^1$H-NMR (CDCl$_3$); δ ppm: 1.50–1.65 (1H, m), 1.80–2.05 (5H, m), 2.45–2.60 (1H, m), 2.65–3.05 (8H, m), 3.45–3.55 (4H, m), 3.90–4.00 (2H, m), 4.55–4.65 (3H, m), 6.62 (1H, d, J=2.6 Hz), 6.71 (1H, dd, J=8.4, 2.6 Hz), 6.87 (1H, d, J=8.1 Hz), 6.98 (1H, d, J=8.4 Hz), 7.05–7.15 (2H, m); Specific rotation: $[α]_D^{25}$=−54.7° (c=0.57, MeOH)

(−)-1-[2-[(2S)-2-[[(2R)-2-Hydroxy-2-[4-hydroxy-3-(2-hydroxyethyl)phenyl]ethyl]amino]-1,2,3,4-tetrahydronaphthalen-7-yloxy]acetyl]piperidine (Compound 17)

Using (−)-1-[2-[(2S)-2-[[(2R)-2-[4-benzyloxy-3-(2-benzyloxyethyl)phenyl]-2-hydroxyethyl]amino]-1,2,3,4-tetrahydronaphthalen-7-yloxy]acetyl]piperidine obtained in Reference Example 9, the procedure of Example 5 was repeated to give amorphous (−)-1-[2-[(2S)-2-[[(2R)-2-hydroxy-2-[4-hydroxy-3-(2-hydroxyethyl)phenyl]ethyl]amino]-1,2,3,4-tetrahydronaphthalen-7-yloxy]acetyl]

piperidine (Compound 17). This amorphous becomes a crystalline form having a melting point of 162 to 165° C. when recrystallized using tetrahydrofuran as a solvent.

IR (KBr): 3388, 1640 cm$^{-1}$; $^1$H-NMR (CDCl$_3$); δ ppm: 1.30–1.90 (9H, m), 2.00–2.10 (1H, m), 2.45–2.60 (1H, m), 2.65–3.10 (9H, m), 3.40–3.65 (4H, m), 3.98 (2H, dd, J=5.8, 4.8 Hz), 4.55–4.65 (3H, m), 6.63 (1H, d, J=2.8 Hz), 6.71 (1H, dd, J=8.5, 2.8 Hz), 6.89 (1H, d, J=8.1 Hz), 6.95–7.15 (3H, m); Specific rotation: $[α]_D^{30}$=−39.2° (c=0.50, CHCl$_3$)

(−)-4-[2-[(2S)-2-[[(2R)-2-Hydroxy-2-[4-hydroxy-3-(2-hydroxyethyl)phenyl]ethyl]amino]-1,2,3,4-tetrahydronaphthalen-7-yloxy]acetyl]morpholine (Compound 18)

Using (−)-4-[2-[(2S)-2-[[(2R)-2-[4-benzyloxy-3-(2-benzyloxyethyl)phenyl]-2-hydroxyethyl]amino]-1,2,3,4-tetrahydronaphthalen-7-yloxy]acetyl]morpholine obtained in Reference Example 9, the procedure of Example 5 was repeated to give amorphous (−)-4-[2-[(2S)-2-[[(2R)-2-hydroxy-2-[4-hydroxy-3-(2-hydroxyethyl)phenyl]amino]-1,2,3,4-tetrahydronaphthalen-7-yloxy]acetyl]morpholine (Compound 18). This amorphous becomes a crystalline form having a melting point of 119 to 122° C. when recrystallized using acetone as a solvent.

IR (KBr): 3353, 1651 cm$^{-1}$; $^1$H-NMR (CDCl$_3$); δ ppm: 1.50–1.70 (2H, m), 2.00–2.10 (1H, m), 2.50–3.10 (10H, m), 3.50–3.75 (8H, m), 3.95–4.00 (2H, m), 4.55–4.70 (3H, m), 6.63 (1H, d, J=2.8 Hz), 6.71 (1H, dd, J=8.3, 2.8 Hz), 6.89 (1H, d, J=8.2 Hz), 6.95–7.15 (3H, m); Specific rotation: $[α]_D^{29}$=−60.8° (c=0.50, CHCl$_3$)

Example 7

(−)-2-[(2S)-2-[[(2R)-2-Hydroxy-2-(4-hydroxy-3-hydroxymethylphenyl)ethyl]amino]-1,2,3,4-tetrahydronaphthalen-7-yloxy]-N,N-dimethylacetamide 0.5 sulfate (Compound 19)

(−)-2-[(2S)-2-[[(2R)-2-Hydroxy-2-(4-hydroxy-3-hydroxymethylphenyl)ethyl]amino]-1,2,3,4-tetrahydronaphthalen-7-yloxy]-N,N-dimethylacetamide (Compound 6) (600 mg) was suspended in 70 ml of ethanol, 1.45 ml of 1 N aqueous sulfuric acid solution was added to the suspension, and the mixture was heated to dissolve the compound. After cooling, the precipitated crystals were collected by filtration to give 649 mg of (−)-2-[(2S)-2-[[(2R)-2-hydroxy-2-(4-hydroxy-3-hydroxymethylphenyl)ethyl]amino]-1,2,3,4-tetrahydronaphthalen- 7-yloxy]-N,N-dimethylacetamide 0.5 sulfate (Compound 19) having a melting point of 195 to 199° C.

IR (KBr): 3420, 1640 cm$^{-1}$; $^1$H-NMR (DMSO-d$_6$); δ ppm: 1.55–1.70 (1H, m), 2.00–2.15 (1H, m), 2.55–3.25 (13H, m), 4.48 (2H, s), 4.65–4.80 (3H, m), 5.00 (1H, br), 6.63 (1H, d, J=2.6 Hz), 6.67 (1H, dd, J=8.4, 2.6 Hz), 6.73 (1H, d, J=8.2 Hz), 6.96 (1H, d, J=8.4 Hz), 7.06 (1H, dd, J=8.2, 2.0 Hz), 7.33 (1H, d, J=2.0 Hz), 9.30 (1H, br); Specific rotation: $[α]_D^{28}$=−69.8° (c=0.52, H$_2$O)

Example 8

Using (−)-2-[(2S)-2-[[(2R)-2-hydroxy-2-(4-hydroxy-3-hydroxymethylphenyl)ethyl]amino]-1,2,3,4-tetrahydronaphthalen-7-yloxy]-N,N-dimethylacetamide (Compound 6) and L-tartaric acid or D-tartaric acid, the following salts were obtained in the same manner as that described in Example 7.

(−)-2-[(2S)-2-[[(2R)-2-Hydroxy-2-(4-hydroxy-3-hydroxymethylphenyl)ethyl]amino]-1,2,3,4-tetrahydronaphthalen-7-yloxy]-N,N-dimethylacetamide 0.5 L-tartrate (Compound 20)

Melting point: 109–115° C. (recrystallization solvent: ethanol) IR (KBr): 3350, 1646, 1614 cm$^{-1}$; $^1$H-NMR (DMSO-d$_6$); δ ppm: 1.55–1.70 (1H, m), 2.00–2.15 (1H, m), 2.60–3.25 (13H, m), 3.85 (1H, s), 4.48 (2H, s), 4.65–4.80 (3H, m), 6.64 (1H, d, J=2.6 Hz), 6.67 (1H, dd, J=8.4, 2.6 Hz), 6.73 (1H, d, J=8.2 Hz), 6.96 (1H, d, J=8.4 Hz), 7.06 (1H, dd, J=8.2, 2.0 Hz), 7.33 (1H, d, J=2.0 Hz); Specific rotation: $[α]_D^{28}$=−56.4° (c=0.50, H$_2$O)

(−)-2-[(2S)-2-[[(2R)-2-Hydroxy-2-(4-hydroxy-3-hydroxymethylphenyl)ethyl]amino]-1,2,3,4-tetrahydronaphthalen-7-yloxy]-N,N-dimethylacetamide 0.5 D-tartrate (Compound 21)

Melting point: 123–124° C. (recrystallization solvent: ethanol) IR (KBr): 3400, 1645, 1613 cm$^{-1}$; $^1$H-NMR (DMSO-d$_6$); δ ppm: 1.55–1.70 (1H, m), 2.00–2.15 (1H, m), 2.60–3.25 (13H, m), 3.84 (1H, s), 4.48 (2H, s), 4.65–4.80 (3H, m), 6.64 (1H, d, J=2.6 Hz), 6.67 (1H, dd, J=8.4, 2.6 Hz), 6.73 (1H, d, J=8.2 Hz), 6.96 (1H, d, J=8.4 Hz), 7.06 (1H, dd, J=8.2, 2.0 Hz), 7.33 (1H, d, J=2.0 Hz); Specific rotation: $[α]_D^{28}$=−68.5° (c=0.52, H$_2$O)

Using (−)-1-[2-[(2S)-2-[[(2R)-2-hydroxy-2-(4-hydroxy-3-hydroxymethylphenyl)ethyl]amino]-1,2,3,4-tetrahydronaphthalen-7-yloxy]acetyl]pyrrolidine (Compound 7) and sulfuric acid, L-tartaric acid or D-tartaric acid, the following salts were obtained in the same manner as that described in Example 7.

(−)-1-[2-[(2S)-2-[[(2R)-2-Hydroxy-2-(4-hydroxy-3-hydroxymethylphenyl)ethyl]amino]-1,2,3,4-tetrahydronaphthalen-7-yloxy]acetyl]pyrrolidine 0.5 sulfate (Compound 22)

Melting point: 169–172° C. (recrystallization solvent: ethanol) IR (KBr): 3400, 1640 cm$^{-1}$; $^1$H-NMR (DMSO-d$_6$); δ ppm: 1.55–1.95 (5H, m), 2.00–2.15 (1H, m), 2.55–3.50 (11H, m), 4.48 (2H, s), 4.63 (2H, s), 4.72 (1H, dd, J=9.6, 3.1 Hz), 4.99 (1H, br), 6.64 (1H, d, J=2.6 Hz), 6.68 (1H, dd, J=8.4, 2.6 Hz), 6.73 (1H, d, J=8.2 Hz), 6.96 (1H, d, J=8.4 Hz), 7.06 (1H, dd, J=8.2, 2.0 Hz), 7.33 (1H, d, J=2.0 Hz), 9.31 (1H, br); Specific rotation: $[α]_D^{28}$=−67.7° (c=0.52, H$_2$O)

(−)-1-[2-[(2S)-2-[[(2R)-2-Hydroxy-2-(4-hydroxy-3-hydroxymethylphenyl)ethyl]amino]-1,2,3,4-tetrahydronaphthalen-7-yloxy]acetyl]pyrrolidine 0.5 L-tartrate (Compound 23)

Melting point: 130–134° C. (recrystallization solvent: ethanol) IR (KBr): 3400, 1635, 1614 cm$^{-1}$; $^1$H-NMR (DMSO-d$_6$); δ ppm: 1.55–1.95 (5H, m), 2.00–2.15 (1H, m), 2.55–3.25 (7H, m), 3.30 (2H, t, J=6.9 Hz), 3.40–3.50 (2H, m), 3.86 (1H, s), 4.48 (2H, s), 4.63 (2H, s), 4.65–4.75 (1H, m), 6.64 (1H, d, J=2.5 Hz), 6.68 (1H, dd, J=8.4, 2.5 Hz), 6.73 (1H, d, J=8.2 Hz), 6.97 (1H, d, J=8.4 Hz), 7.06 (1H, dd, J=8.2, 2.0 Hz), 7.33 (1H, d, J=2.0 Hz); Specific rotation: $[α]_D^{28}$=−53.4° (c=0.55, H$_2$O)

(−)-1-[2-[(2S)-2-[[(2R)-2-Hydroxy-2-(4-hydroxy-3-hydroxymethylphenyl)ethyl]amino]-1,2,3,4-tetrahydronaphthalen-7-yloxy]acetyl]pyrrolidine 0.5 D-tartrate (Compound 24)

Melting point: 130–134° C. (recrystallization solvent: ethanol) IR (KBr): 3400, 1635, 1614 cm$^{-1}$; $^1$H-NMR (DMSO-d$_6$); δ ppm: 1.55–1.95 (5H, m), 2.00–2.20 (1H, m), 2.55–3.25 (7H, m), 3.30 (2H, t, J=6.8 Hz), 3.44 (2H, t, J=6.8 Hz), 3.85 (1H, s), 4.48 (2H, s), 4.63 (2H, s), 4.70 (1H, dd, J=9.2, 2.8 Hz), 6.64 (1H, d, J=2.6 Hz), 6.68 (1H, dd, J=8.3, 2.6 Hz), 6.73 (1H, d, J=8.2 Hz), 6.97 (1H, d, J=8.3 Hz), 7.06 (1H, dd, J=8.2, 2.0 Hz), 7.33 (1H, d, J=2.0 Hz); Specific rotation: $[α]_D^{28}$=−66.2° (c=0.53, H$_2$O)

Example 9

Using (−)-2-[(2S)-2-[[(2R)-2-hydroxy-2-[4-hydroxy-3-(2-hydroxyethyl)phenyl]ethyl]amino]-1,2,3,4- tetrahydronaphthalen-7-yloxy]-N,N-dimethylacetamide (Compound 13) and sulfuric acid, the following salt was obtained in the same manner as that described in Example 7. (−)-2-[(2S)-2-[[(2R)-2-Hydroxy-2-[4-hydroxy-3-(2-hydroxyethyl)phenyl]ethyl]amino]-1,2,3,4-tetrahydronaphthalen-7-yloxy]-N,N-dimethylacetamide 0.5 sulfate (Compound 25)

Melting point: 211–215° C. (decomposition) (recrystallization solvent: water); IR (KBr) : 3418, 1636 cm$^{-1}$; $^1$H-NMR (DMSO-d$_6$); δ ppm: 1.55–1.75 (1H, m), 2.05–2.15 (1H, m), 2.60–3.25 (15H, m), 3.56 (2H, t, J=7.3 Hz), 4.60–4.80 (3H, m), 6.62 (1H, d, J=2.6 Hz), 6.67 (1H, dd, J=8.4, 2.6 Hz), 6.75 (1H, d, J=8.2 Hz), 6.96 (1H, d, J=8.4 Hz), 7.03 (1H, dd, J=8.2, 2.1 Hz), 7.09 (1H, d, J=2.1 Hz), 9.25 (1H, br); Specific rotation: $[\alpha]_D^{25}$=−70.8° (c=1.0, H$_2$O)

Using (−)-4-[2-[(2S)-2-[[(2R)-2-hydroxy-2-(4-hydroxy-3-(2-hydroxyethyl)phenyl]ethyl]amino]-1,2,3,4-tetrahydronaphthalen-7-yloxy]acetyl]morpholine (Compound 18) and sulfuric acid, the following salt was obtained in the same manner as that described in Example 7. (−)-4-[2-[(2S)-2-[[(2R)-2-Hydroxy-2-(4-hydroxy-3-(2-hydroxyethyl)phenyl]ethyl]amino]-1,2,3,4-tetrahydronaphthalen-7-yloxy]acetyl]morpholine 0.5 sulfate (Compound 26)

Melting point: 129–134° C. (decomposition) (recrystallization solvent: isopropanol-ethanol); IR (KBr): 3394, 1648 cm$^{-1}$; $^1$H-NMR (DMSO-d$_6$); δ ppm: 1.50–1.75 (1H, m), 2.00–2.15 (1H, m), 2.40–3.90 (19H, m), 4.60–4.85 (3H, m), 6.60–6.80 (3H, m), 6.97 (1H, d, J=7.9 Hz), 7.03 (1H, dd, J=8.4, 2.0 Hz), 7.08 (1H, d, J=1.5 Hz), 9.25 (1H, br); Specific rotation: $[\alpha]_D^{25}$=−58.3° (c=0.60, MeOH)

Test Example 1
Action of drugs on the spontaneous contractions of isolated myometria The uterus of a pregnant SD rat (pregnancy day of 21) was isolated and longitudinal uterine muscle strips (about 15 mm in length and about 5 mm in width) free from the basal plate were prepared. The experiment was conducted according to the Magnus method. The preparations were mounted with a tension of 1 g in Locke-Ringer solution maintained at 37° C. and gassed with a mixture of 95% of oxygen and 5% of carbon dioxide. Spontaneous contractions of the myometrium were induced isometrically via a pressure transducer and recorded on a rectigram. The efficacy was evaluated by comparing the total degree of uterine contraction during 5 minutes before the addition of the drug with the total degree of uterine contraction during 5 minutes after the addition of the drug and calculating the 50% inhibitory concentration as EC$_{50}$.

Test Example 2
Action of drugs on the atrial contractions of isolated atria

The atria of SD male rats (350 to 400 g in body weight) were isolated and the experiment was conducted according to the Magnus method. The preparations were mounted with a tension of 1 g in Krebs-Henseleit solution maintained at 37° C. and gassed with a mixture of 95% of oxygen and 5% of carbon dioxide. The atrial contraction was induced isometrically via a pressure transducer and recorded on a rectigram. After addition of the drug, its efficacy was evaluated by calculating EC$_{20}$ value which is the drug concentration which increases 20 beats per minute of heart rate.

Test Example 3
Acute Toxicity

To 5 male ICR mice of 4 weeks age was administered intravenously 2-[(2S)-2-[[(2R)-2-hydroxy-2-(4-hydroxy-3hydroxymethylphenyl)ethyl]amino]-1,2,3,4-tetrahydronaphthalen-7-yloxy]-N,N-dimethylacetamide 0.5 sulfate in saline at dose of 20 mg/kg. No death of animals was observed during 24 hours after the administration.

We claim:
1. A 3,4-disubstituted phenylethanolaminotetralin-carboxamide compound represented by the general formula:

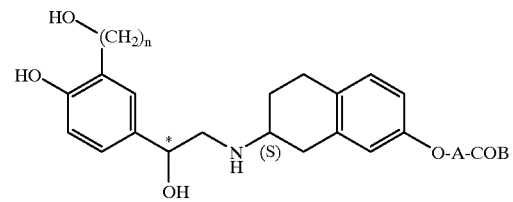

wherein A represents a lower alkylene group; B represents an amino group, a di(lower alkyl)amino group or a 3 to 7-membered alicyclic amino group which may contain an oxygen atom in the ring; n is an integer of 1 or 2; the carbon atom marked with * represents a carbon atom in an R configuration, an S configuration or a mixture thereof; and the carbon atom marked with (S) represents a carbon atom in an S configuration or a pharmaceutically acceptable salt thereof.

2. The 3,4-disubstituted phenylethanolaminotetralin-carboxamide compound as claimed in claim 1, represented by the general formula:

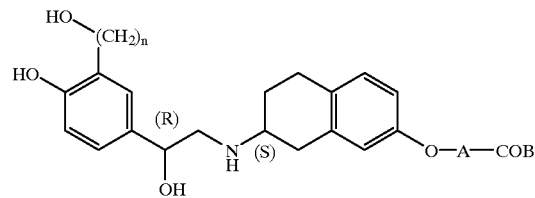

wherein A represents a lower alkylene group; B represents an amino group, a di(lower alkyl)amino group or a 3 to 7-membered alicyclic amino group which may contain an oxygen atom in the ring; n is an integer of 1 or 2; the carbon atom marked with (R) represents a carbon atom in an R configuration; and the carbon atom marked with (S) represents a carbon atom in an S configuration or a pharmaceutically acceptable salt thereof.

3. The 3,4-disubstituted phenylethanolaminotetralin-carboxamide compound as claimed in claim 2, represented by the formula:

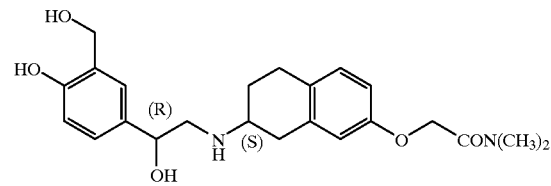

wherein the carbon atom marked with (R) represents a carbon atom in an R configuration; and the carbon atom marked with (S) represents a carbon atom in an S configuration or a pharmaceutically acceptable salt thereof.

4. The 3,4-disubstituted phenylethanolaminotetralin-carboxamide compound as claimed in claim 2, represented by the formula:

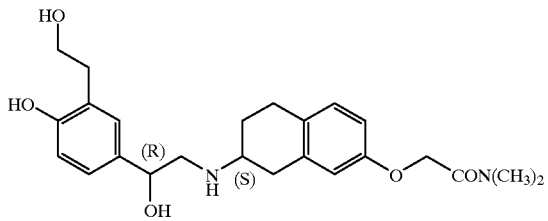

wherein the carbon atom marked with (R) represents a carbon atom in an R configuration; and the carbon atom marked with (S) represents a carbon atom in an S configuration or a pharmaceutically acceptable salt thereof.

5. A pharmaceutical composition which comprises
(a) a 3,4-disubstituted phenylethanolaminotetralin-carboxamide compound represented by the general formula:

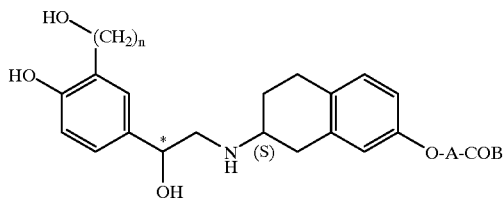

wherein A represents a lower alkylene group; B represents an amino group, a di(lower alkyl)amino group or a 3 to 7-membered alicyclic amino group which may contain an oxygen atom in the ring; n is an integer of 1 or 2; the carbon atom marked with * represents a carbon atom in an R configuration, an S configuration or a mixture thereof; and the carbon atom marked with (S) represents a carbon atom in an S configuration or a pharmaceutically acceptable salt thereof, and
(b) a pharmaceutically acceptable carrier or diluent.

6. A pharmaceutical composition as claimed in claim 5, which comprises
(a) a 3,4-disubstituted phenylethanolaminotetralin-carboxamide compound represented by the general formula:

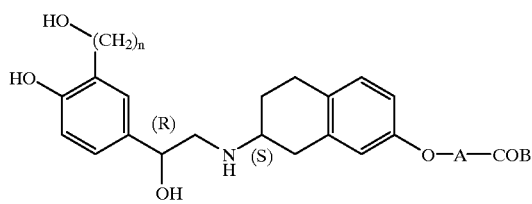

wherein A represents a lower alkylene group; B represents an amino group, a di(lower alkyl)amino group or a 3 to 7-membered alicyclic amino group which may contain an oxygen atom in the ring; n is an integer of 1 or 2; the carbon atom marked with (R) represents a carbon atom in an R configuration; and the carbon atom marked with (S) represents a carbon atom in an S configuration or a pharmaceutically acceptable salt thereof, and
(b) a pharmaceutically acceptable carrier or diluent.

7. A pharmaceutical composition as claimed in claim 6, the 3,4-disubstituted phenylethanolaminotetralin-carboxamide compound is represented by the formula:

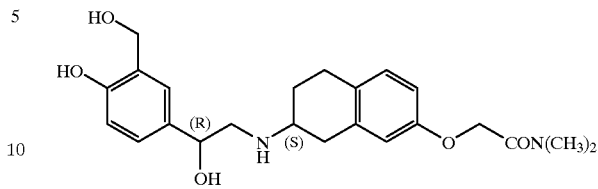

wherein the carbon atom marked with (R) represents a carbon atom in an R configuration; and the carbon atom marked with (S) represents a carbon atom in an S configuration or a pharmaceutically acceptable salt thereof.

8. A pharmaceutical composition as claimed in claim 6, wherein the 3,4-disubstituted phenylethanolaminotetralin-carboxamide compound is represented by the formula:

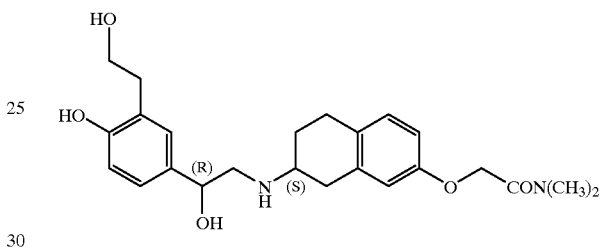

wherein the carbon atom marked with (R) represents a carbon atom in an R configuration; and the carbon atom marked with (S) represents a carbon atom in an S configuration or a pharmaceutically acceptable salt thereof.

9. A method for the prevention of threatened abortion and premature labor, the prevention and treatment of diseases associated with bronchiostenosis and airway obstruction, or pain remission and stone removal in urolithiasis which comprises administering a 3,4-disubstituted phenylethano-laminotetralincarboxamide compound represented by the general formula:

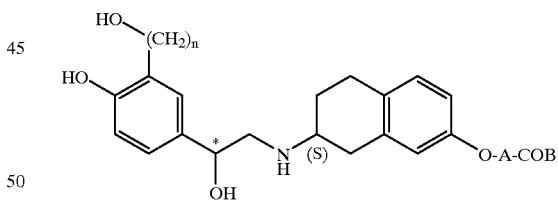

wherein A represents a lower alkylene group; B represents an amino group, a di(lower alkyl)amino group or a 3 to 7-membered alicyclic amino group which may contain an oxygen atom in the ring; n is an integer of 1 or 2; the carbon atom marked with * represents a carbon atom in an R configuration, an S configuration or a mixture thereof; and the carbon atom marked with (S) represents a carbon atom in an S configuration or a pharmaceutically acceptable salt thereof.

10. A method for prevention of threatened abortion and premature labor, for prevention and treatment of diseases associated with bronchiostenosis and airway obstruction, and for pain remission and stone removal in urolithiasis comprising administering to a subject in need of same a therapeutically effective amount of a 3,4-disubstituted phenylethanolaminotetralincarboxamide compound represented by the general formula:

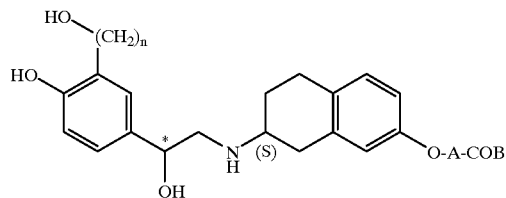

wherein A represents a lower alkylene group; B represents an amino group, a di(lower alkyl)amino group or a 3 to 7-membered alicyclic amino group which may contain an oxygen atom in the ring; n is an integer of 1 or 2; the carbon atom marked with * represents a carbon atom in an R configuration, an S configuration or a mixture thereof; and the carbon atom marked with (S) represents a carbon atom in an S configuration or pharmaceutically acceptable salt thereof.

* * * * *